US008994534B2

United States Patent
Zhu et al.

(10) Patent No.: US 8,994,534 B2
(45) Date of Patent: Mar. 31, 2015

(54) DOCUMENTS MANAGEMENT USING REMOTE DOCUMENT LOCATION AND RETRIEVAL

(75) Inventors: Shengbo Zhu, San Jose, CA (US); Su Shiong Huang, Bellevue, WA (US)

(73) Assignee: ZMicrodata Corporation, San Jose, CA (US)

( * ) Notice: Subject to any disclaimer, the term of this patent is extended or adjusted under 35 U.S.C. 154(b) by 704 days.

(21) Appl. No.: 12/803,712

(22) Filed: Jul. 2, 2010

(65) Prior Publication Data

US 2012/0001758 A1     Jan. 5, 2012

(51) Int. Cl.
*G08B 13/14* (2006.01)
*G08B 21/00* (2006.01)
*B65D 27/00* (2006.01)
*G06Q 10/10* (2012.01)
*G06F 19/00* (2011.01)

(52) U.S. Cl.
CPC .............. *G06Q 10/10* (2013.01); *G06F 19/322* (2013.01)
USPC ..... 340/572.8; 340/570; 340/540; 340/572.2; 229/67.1

(58) Field of Classification Search
CPC ........................ G08B 13/1427; G06K 17/00
USPC .................... 340/570, 572.1, 815.4, 9.1–9.17
See application file for complete search history.

(56) References Cited

U.S. PATENT DOCUMENTS

| | | | | |
|---|---|---|---|---|
| 5,158,347 A * | 10/1992 | Warren et al. | | 312/319.8 |
| 5,450,070 A * | 9/1995 | Massar et al. | | 340/8.1 |
| 5,689,238 A * | 11/1997 | Cannon et al. | | 340/572.1 |
| 5,721,531 A * | 2/1998 | Garver et al. | | 340/8.1 |
| 5,739,765 A * | 4/1998 | Stanfield et al. | | 340/8.1 |
| 5,805,074 A * | 9/1998 | Warren et al. | | 340/5.54 |
| 5,936,527 A * | 8/1999 | Isaacman et al. | | 340/572.1 |
| 5,977,875 A * | 11/1999 | Lin et al. | | 340/570 |
| 6,348,864 B1 * | 2/2002 | Lin et al. | | 340/570 |
| 7,113,095 B2 * | 9/2006 | Kuzma et al. | | 340/572.7 |
| 2004/0044956 A1 * | 3/2004 | Huang | | 715/511 |
| 2004/0202386 A1 * | 10/2004 | Quine | | 382/305 |
| 2007/0086061 A1 * | 4/2007 | Robbins | | 358/400 |
| 2008/0197175 A1 * | 8/2008 | Christensen et al. | | 229/67.1 |
| 2009/0166400 A1 * | 7/2009 | Lee | | 229/67.3 |

\* cited by examiner

*Primary Examiner* — Daniell L Negron
*Assistant Examiner* — Mohamed Barakat

(57) ABSTRACT

A documents management system with remote location and retrieval of documents contained in file folders positioned in file drawers in a collection of file cabinets. Each document has an RFID tag containing a document identifier and the contents of the document stored in a read-only memory. Each file folder has a circuit containing a unique identifier for that folder. Each file cabinet has a control unit which searches for a specific file folder in response to receipt of a file folder request from a source. If the folder is found, each cabinet has an R.F. reader which searches for a specific document in response to receipt of a document request from the source. If the document is found, the R.F. reader extracts the document contents and transmits them to the source.

12 Claims, 23 Drawing Sheets

US 8,994,534 B2

DOCUMENTS MANAGEMENT USING REMOTE DOCUMENT LOCATION AND RETRIEVAL

BACKGROUND OF THE INVENTION

This invention relates to documents management in general, and in particular to an improved documents management technique using remote document location and retrieval.

In medical records, legal and business offices, and some homes, file storage cabinets are typically used to store documents used for medical, legal, other business and personal purposes. A typical file storage cabinet has several pull-out drawers each containing a relatively large number of file folders, with each folder containing one or more documents. In order to enable the documents contained in the various file folders to be readily accessed, some type of documents management system is necessary.

Documents management is typically performed by file folder management. Each document is initially assigned to, and placed in, an identified file folder dedicated to documents of a particular subject matter (e.g., "utility bills for a specific account"). Later generated related documents are typically assigned to and placed in this same file folder.

File folder management is typically conducted by providing each file folder with a tab portion visible when the file drawer is opened (usually along the upper edge of the folder) and containing readable information describing the content of the file folder. The readable information is typically a short form of identification, such as an account name, a subject name (e.g., "Bank Statements") or the like.

In order to provide ready access to the individual documents contained in the file folders, some type of indexing arrangement is normally used to identify the file cabinet drawer location of each file folder. A simple technique commonly employed is an alphabetical index card placed on the front panel of each drawer in a file cabinet listing the file folders in alphabetical order. For example, one file drawer panel might have an index card listing file folders starting with the letters A-F, another drawer might have an index card listing file folders starting with the letters G-L, etc. Frequently, more sophisticated indexing arrangements are used, such as a computer-based index listing all file folders by a short form identifier and a corresponding enlarged and more thorough description of the file folder contents. Even such computer-based arrangements still require the use of a readable tab or tag on each file folder in order to identify a given file folder to a user. This is highly undesirable, since it facilitates the search by any unauthorized user for a specific file folder name or for a file folder containing information of a particular type. Nevertheless, known file folder management systems require the use of visible tabs or tags in order for the files to be reasonably locatable.

In those applications in which several individuals have access to the file drawer contents of some or all of the file cabinets, some arrangement is usually made to monitor the disposition of the file folders. For example, in a business application, it is convenient and sometimes necessary to provide a sign out and return procedure so that the whereabouts of a given file folder will always be known. Usually, such monitoring attempts fail to accurately track the file folders because of the failure of individuals to faithfully follow the procedure. Consequently, at any given time, the integrity of the file management system can only be verified by actually looking through each file drawer and checking the file folders and their contents with the master index. This requirement is both time-consuming and burdensome, and thus a severe disadvantage.

In known file management systems of the type described above, once a file folder is provided with a contents identifier, that file folder is permanently associated with the nature of its contents. To change the contents to some other category, the file folder must either be thrown away and a new, unmarked file folder substituted in its place, or the identification label must be changed. In addition, the master index must be updated, either manually or by using the computer in a computer-based indexing system. These procedures are not always followed by office personnel, and the integrity of the file system is consequently compromised.

In all examples of known file management systems, the file folders are usually provided with some type of human readable or machine readable identification indicia, such as a label or tag affixed to the upper margin of each file folder. In more sophisticated systems, a computer is used to assist in keeping track of the objects. When a file folder is removed from the usual location, some procedure is typically used to note the fact that that file folder has been removed from its normal location. This is accomplished either by operator entry of the change into the system computer, or by using tag or label reading devices (e.g., bar code readers) to enter the information into the system computer.

U.S. Pat. No. 5,977,875 issued Nov. 2, 1999 for "Collective Objects Management System Using R.F. Object Identification", the disclosure of which is hereby incorporated by reference, discloses an example of a file folder management system which eliminates the disadvantages noted above with previously known file folder management systems. In addition, the file folder management system disclosed in the '875 U.S. patent provides a simple and efficient way to find a desired file folder stored somewhere in a large collection of different file folders. The system disclosed in the '875 U.S. patent uses R.F. sensitive circuits to maintain control of all file folders in a collection. Each file folder has an associated R.F. sensitive circuit which resonates at a unique frequency when an R.F. signal at that unique frequency is received by the circuit, and an indicator coupled to the R.F. circuit for identifying the file folder to a human operator. The indicator is preferably a visible indicator—such as an LED—coupled to the file folder in a convenient location which can readily be seen by a human operator when a file drawer is opened. Alternatively, an audible indicator—such as a buzzer—can be used.

More specifically, the folder circuit included in each file folder to be placed in a file drawer has a crystal responsive to a particular R.F. frequency, with the resonant frequency of a given crystal different from all the other crystals. Each file folder circuit is electrically coupled to a drawer signal input/output using the electrically conductive upper support rails usually found in conventional file cabinets. One of the rails is modified by electrically isolating that rail from the remaining electrically conductive elements in the drawer. Each drawer is provided with an indicator, preferably a flashing LED visible indicator, mounted on the front panel of the drawer. A current detector circuit is used to control the state of the drawer panel indicator.

All drawer input/output terminals are electrically coupled in parallel to an associated host computer, either using dedicated connectors (i.e., hard wired) or transceivers (i.e., wireless communication). The host computer includes an R.F. signal generator capable of generating signals matching all the crystal frequencies. To find a file folder, a user specifies that file folder to the computer, typically by using a keyboard or a mouse. The computer causes the R.F. signal generator to generate an R.F. signal whose frequency matches that of the crystal in the specified file folder. The R.F. signal is transmitted to all the file cabinets in the system, and thus to all the file drawers. If the specified file folder is located in any one of the drawers, the indicator on the front panel of the drawer containing that file folder, and the indicator of the correct file folder, are both activated. The user then opens the drawer with the active panel indicator and removes the file folder with the active file folder indicator. The file management system disclosed in the '875 U.S. patent eliminates the need for readable tabs or tags on each file folder, since the correct file folder is designated by the activated indicator. Also, the nature of a file folder can be changed by simply entering the necessary information into the computer. In addition, the integrity of the entire file system can be checked by using an R.F. sweep frequency generator to sweep the entire frequency range of crystal frequencies and detecting any frequency for which a resonant response is absent. The system can be readily and conveniently incorporated into existing file cabinets having the electrically conductive dual rail folder support mechanism.

Commonly assigned co-pending U.S. patent application Ser. No. 12/586,5521, filed 09/24/2009 for "Collective Objects Management System With Object Identification Using Multiple Crystals" discloses an improvement over the '875 technique in which the file folder circuits are provided with two or more crystals and each file cabinet includes an R.F. generator. In this improved technique, a file folder is specified by generating an R.F. signal having a number of frequency components equal to the number of crystals in the file folder circuit.

Commonly assigned co-pending U.S. patent application Ser. No. 12/802,645, filed Jun. 12, 2010 for "Collective Objects Management System With Object Identification Using Addressable Decoder Units" discloses another example of a file folder management system which eliminates the disadvantages noted above with previously known file management systems. In addition, like the '875 system, the file management system disclosed in the '645 U.S. patent application provides a simple and efficient way to find an individual file folder stored somewhere in a large collection of different file folders. The system disclosed in the '645 U.S. patent application uses addressable decoder units to maintain control of all file folders in a collection. Each file folder has an associated addressable decoder unit with a unique address in the file folder management system which responds to the receipt of that unique address from a source. The source is a local encoder in the file cabinet containing the addressed file, which generates the unique address in response to the receipt of a file folder identification signal from a remote host computer. Each file folder also has an indicator coupled to the decoder unit for identifying the file to a human operator. The indicator is preferably a visible indicator—such as an LED—coupled to the file folder in a convenient location which can readily be seen by a human operator when a file drawer is opened. Alternatively, an audible indicator—such as a buzzer—can be used.

Each file drawer has a plurality of mutually electrically isolated electrically conductive paths, at least one of which can receive address signals supplied by the source and specifying a sought file folder. The file folders positioned in the file drawers each has a plurality of electrically conductive members, each of which is electrically coupled to a different one of the plurality of mutually electrically isolated electrically conductive paths, an address decoder circuit carried by the file folder in the drawer, the address decoder circuit having a unique system address, the address decoder circuit further having a plurality of electrically conductive terminals in electrical contact with the plurality of electrically conductive members, and an indicator, such as a visible indicator (e.g., an LED) coupled to the address decoder circuit for activation whenever the address decoder circuit detects an address signal present on at least one of the plurality of electrically conductive members and representative of the unique system address of that file folder.

Each file cabinet includes an encoder for generating the address signals, the encoder having at least one input terminal for receiving file folder identification signals from a host computer, at least one output terminal coupled to each address decoder circuit of the plurality of file folders, and circuitry for generating a signal representative of the unique system address of the file folder specified by the file folder identification signals from the host computer.

Each file folder has a pair of support braces, with one of the support braces containing the plurality of electrically conductive members. The address decoder circuit and the indicator of each of the file folders are carried by one of the two support braces of each file folder.

The file folder drawer has a front panel with an additional indicator mounted thereon; and the system further includes circuitry for operating the additional indicator whenever an address decoder circuit located in the file folder drawer detects an address signal present on the at least one of the plurality of electrically conductive members and representative of the unique system address of that address decoder.

Each address decoder circuit includes circuitry for generating a VALID signal whenever that address decoder circuit detects an address signal present on the at least one of the plurality of electrically conductive members and representative of the unique system address of that address decoder circuit.

A microcomputer located in the file cabinet supplies power signals to the plurality of file folders via some of the electrically conductive paths, and address signals via the at least one of the electrically conductive paths; and receives VALID signals generated by each address decoder circuit when an incoming address matches a given address decoder circuit system address. The microcomputer also includes circuitry for generating information signals identifying the location in the system of any address decoder circuit which generates a VALID signal. These information signals are transmitted back to the host computer for the purpose of file folder management.

While both of the two techniques for file folder management described above are extremely effective in providing a remote file folder location capability, and remote file folder management, neither provides any capability for remote document location or retrieval. It can frequently occur that a document originally specified to the document management system as being located in a particular file folder is absent from that particular file folder and, in some cases, absent from the entire system, usually due to human error. With known document management systems, this error only becomes known after a human operator—after having been directed to a particular file drawer of a particular cabinet—opens the drawer with the illuminated visible indicator, extracts the file folder with the illuminated visible indicator, inspects the contents of the extracted file folder, and discovers that the specific document sought is missing from the file folder. In such a case, not only has the human operator wasted time in going to the file cabinet; but also it can be most difficult and time consuming to locate the missing document. Other than conducting a physical search of all the file drawer file folders, the system accessibility logs, and personal interviews with all persons suspected of having contact with the missing document, there is no practical way of finding the missing document.

SUMMARY OF THE INVENTION

The invention comprises a documents management system which is devoid of the above-noted disadvantages and which enables remote location and retrieval of documents in a system.

From a process standpoint, the invention comprises a method of remotely locating and retrieving a document physically located in a file folder in a file cabinet in a document storage system having a master list of documents, file folders in which individual documents are registered, and file cabinets in which file folders are located, said method comprising the steps of:

(a) designating a document to be found;
(b) transmitting a file folder request to the file cabinet in which the file folder containing the document is located according to the master list;
(c) locally searching the file cabinet for the file folder identified in the request;
(d) transmitting a file folder found signal to the source of the file folder request when the file folder is found;
(e) transmitting a document identifier signal to the file cabinet containing the found file folder;
(f) locally searching the found file folder for the document specified by the document identifier signal; and
(g) transmitting the contents of the found document to the source of the document identifier signal when the document specified by the document identifier signal has been found.

The step (a) of designating is preferably performed by keyboard entry of the document designation information into a system host computer containing the master list.

The step (b) of transmitting a file folder request is performed over a communication link, which can be wireless or a hard link.

The step (c) of locally searching for a given file folder can be performed using an R.F. search technique or an address matching search technique. For the R.F. search technique, each file folder is provided with a circuit having one or more crystals with a unique resonant frequency, and the file folder search is conducted by generating R.F. search signals having frequency components matching the resonant frequencies of the crystals located in the file folder identified in the request. For the address matching search technique, each file folder is provided with a circuit having an address decoder unit with a unique address permanently stored therein, and the file folder search is conducted by generating address signals having an address value matching the value of the address stored in a decoder circuit located in the file folder identified in the request.

Once the desired file folder has been located, a search for the sought document is conducted. Each document includes an RFID tag with a read-only-memory containing a document identifier and an electronic version of the document. The step (f) of locally searching is performed by using an RFID reader unit and an RFID reader antenna to generate R.F. frequency document tag interrogation signals containing the document identifier. When the document has been located, the RFID reader reads out the entire document contents and transmits this information to the source for follow-on use.

From an apparatus standpoint, the invention comprises a document management system for enabling remote location and retrieval of documents, the system comprising a plurality of file cabinets having a plurality of file drawers; a plurality of file folders located in the file drawers; and a plurality of documents located in the plurality of file folders.

Each document has an RFID tag containing a document identifier and an electronic copy of the contents of the document.

Each file cabinet has a control unit for receiving file folder request signals from a source, performing a file folder search in response to receipt of a file folder request signal, and sending a response to the source indicating the result of the file folder search.

Each file folder has a circuit responsive to a search initiated by a file folder request signal for generating a response signal when the file folder request signal matches the identity of the file folder.

each file cabinet includes an RFID reader for receiving document request signals from a source, performing a document search in response to receipt of a document request signal, and sending the contents of a found document to the source.

The system may implement either an R.F. file folder search technique or an address matching file folder search technique. For the R.F. file folder search technique, the control unit includes an R.F. signal generator for generating search signals having a frequency component; and each file folder circuit has a crystal with a specific resonant frequency so that the response signal is generated when the frequency component of a search signal matches the resonant frequency of the crystal. For the address matching file folder search technique, the control unit includes an address encoder for generating a file folder address signal in response to the receipt of a file folder request signal; and the file folder circuit has an address decoder containing a unique address so that the response signal is generated when the address signal generated by said address encoder matches the unique address.

The invention facilitates the location of a given document by enabling remote searching of the entire document management system file cabinets. The invention also eliminates the necessity for having a human operator physically retrieve a document from the folder in which it is located. In addition, the invention affords remote inspection of the integrity of the document management system by sequentially generating file folder and document identifiers and noting the presence or absence of a response.

For a fuller understanding of the nature and advantages of the invention, reference should be made to the ensuing detailed description taken in conjunction with the accompanying drawings.

DETAILED DESCRIPTION OF THE PREFERRED EMBODIMENTS

The invention requires that each document to be remotely located in a file folder management system be provided with an RFID tag which can be read locally in a file folder in the drawer of a file cabinet in which the document resides. FIGS. 1-6 illustrate such a document and the technique for preparing such a document. These Figs. and the description thereof are taken from U.S. Patent Application Publication no. US 2004/0044956 A1 published Mar. 4, 2004.

Figure 1:
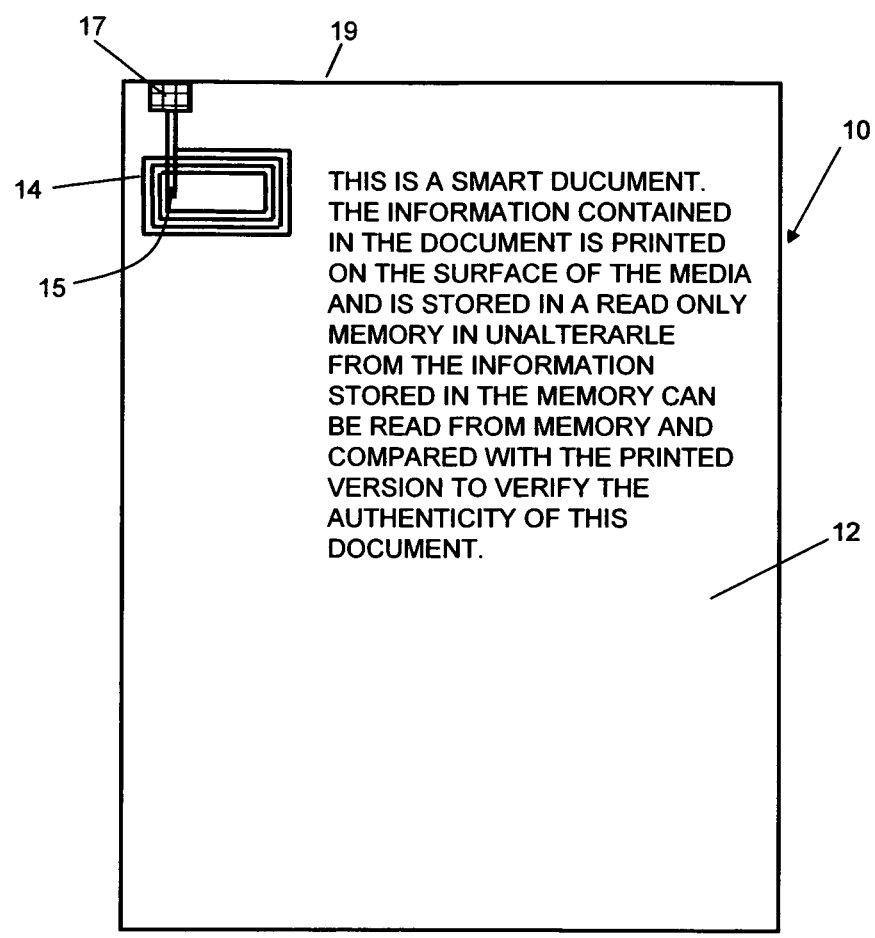
FIG. 1 is a plan view of a document incorporating an RFID tag.

Turning now to the drawings, FIG. 1 is a plan view of a single document in readable sheet form. As seen in this FIG., a document 10 in sheet media form has visible information 12 permanently formed thereon using conventional techniques, such as ink jet printing, laser printing or the equivalent. Although only the obverse side of document 10 is shown in FIG. 1, visible information may also be carried by the reverse side of document 10 to provide a two-sided readable document.

Incorporated into document 10 are a small loop antenna 14 electrically connected to an RFID electronic chip 15. A visible indicator 17, such as a small LED, is preferably attached to document 10 at a physical location at which the state of the indicator 17 can be readily observed when document 10 is stored in a file folder. As seen in FIG. 1, this physical location is adjacent the upper margin 19 of document 10. Visible indicator 17 is electrically connected to RFID chip 15, which controls the state of indicator 17. Visible indicator 17 is preferably a type CMD28-21 SRC surface mount LED currently available from Chicago Miniature Lamp, Inc. Other visible indicators may also be used.

Loop antenna 14 is a multi-turn ohmic conductor formed in any one of several known ways. One such technique is silver paste printing on a polyethylene terephthalate (PET) substrate as disclosed in U.S. Pat. No. 6,373,708 B1 issued Apr. 16, 2002, the disclosure of which is hereby incorporated by reference. Another technique is copper deposition on a substrate as practiced by RCD Technology Corporation of Bethlehem, Pa. The size of the coil (coil diameter and thickness) and the number of turns will be determined by the requirements of a particular application. The function of loop antenna 14 is to provide electromagnetic transfer of information between RFID chip 15 and an RFID reader (described below) located in the file cabinet in which the document resides, as well as to enable inductive transfer of electrical power from the RFID reader to RFID chip 15 to electrically power the active circuit elements within RFID chip 15 and visible indicator 17.

RFID chip 15 may be a commercially available or a custom-designed integrated circuit device having the standard internal functional components commonly found in an RFID (radio frequency identification) integrated circuit. Such standard components include an RF and analog section, a CPU, a ROM and an EEPROM (see 1999 IEEE International Solid-State Circuits Conference publication 0-7803-5129-0/99, FIG. 9.1.1: RFID transponder IC block diagram). RFID chip 15 receives power via loop antenna 14 when interrogated by an outside device, and communicates with the outside device using standard protocols, such as the ISO 14443 protocol, the ISO15693 protocol, or the ISO/IEC 18000-3 Mode 2 protocol. Examples of commercially available RFID chip devices are the PJM Item Tag/Stack Tag available from Infineon Technologies AG of Munich, Germany; and the Tag-it, HF-I Plus, and HF-I Pro transponder tags available from Texas Instruments of Dallas, Tex. The size of RFID chip 15 is on the order of 1.4×1.3 mm, with a thickness of about 0.13 mm. This compares favorably to the average thickness of 0.1 mm for document paper. As will be described more fully below, when a document is being originally prepared, the information to be included in the document is written into the ROM (read-only memory) incorporated into the RFID chip 15. Once this information is written once into the ROM, it cannot be written over or otherwise altered by any interrogation device. Stated differently, once the document has been prepared, RFID chip 15 can be interrogated by the RFID reader and can only supply the document information to the outside device—i.e, it cannot alter the document information stored in the ROM.

Loop antenna 14 and RFID chip 15 are preferably both incorporated into an ID tag, such as that shown and described in U.S. Pat. No. 6,154,137 issued Nov. 28, 2000, the disclosure of which is hereby incorporated by reference. Generally, an ID tag has the antenna and the RFID chip mounted on or encapsulated in a thin substrate, such as the PET substrate noted above. The ID tag is incorporated into the sheet media, which may be paper, plastic material such as Mylar sheet media, or any other known sheet media material used in the preparation of sheet media documents. Incorporation of the ID tag into the sheet media may be done by adhesion to one of the sheet surfaces, bonding within the sheet media material, or by using any other known technique for firmly embedding the thin plastic ID tag into a sheet media material. Once the sheet media has been prepared by incorporating the ID tag, the sheet is ready for preparation of the document.

Figure 2:
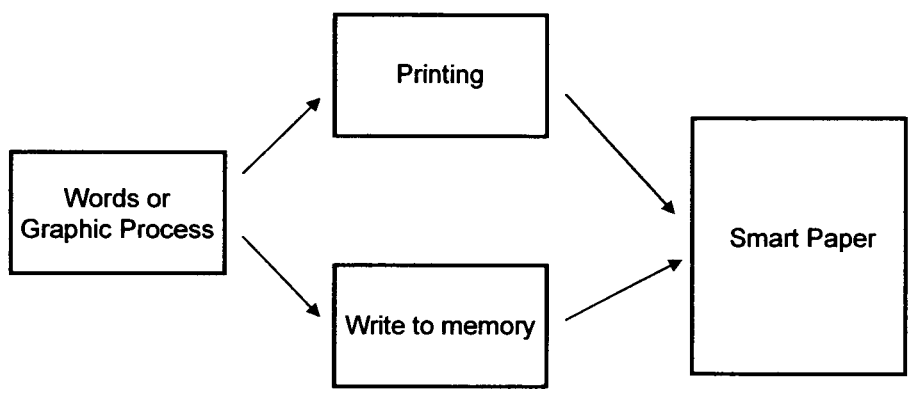
FIG. 2 is a schematic block diagram illustrating a method of preparing the document of FIG. 1.

With reference to FIG. 2, the general process for preparing a document is as follows. The information (which can be text only, graphics only or a combination of the two types) is first composed using a host device, such as a PC, a word processor or any other known device for composing documents. Once the information is composed, it is printed onto one or both sides of the sheet media. The same information is also electromagnetically transferred to the RFID chip and is written into the ROM portion of the RFID chip 15. It is noted that the printing step and the electromagnetic transfer step may both be conducted simultaneously or may be performed sequentially. When both the printing and writing steps are completed, the document is finished, and may be put to its intended purpose. Preferably, the prepared document is verified using the procedure described below before passing the document on for use.

Figure 3:
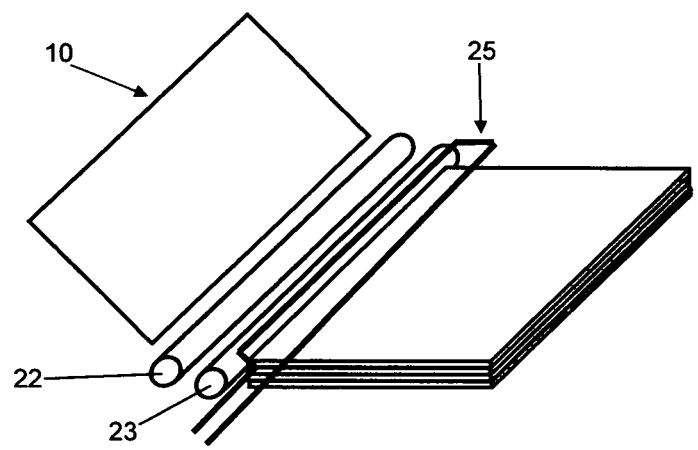
FIG. 3 is a schematic view of a printing device for preparing the document of FIG. 1.

FIG. 3 schematically illustrates a writing device for use in the preparation of a document. As seen in this FIG., a printer having feed rollers 22, 23 receives a blank document sheet 10 and feeds the sheet through a print region (not shown). The printer has a write antenna 25 spanning the width of a document sheet 10 and transmits the electromagnetic version of the information to the RFID chip 15 incorporated into the document sheet 10.

Figure 4:
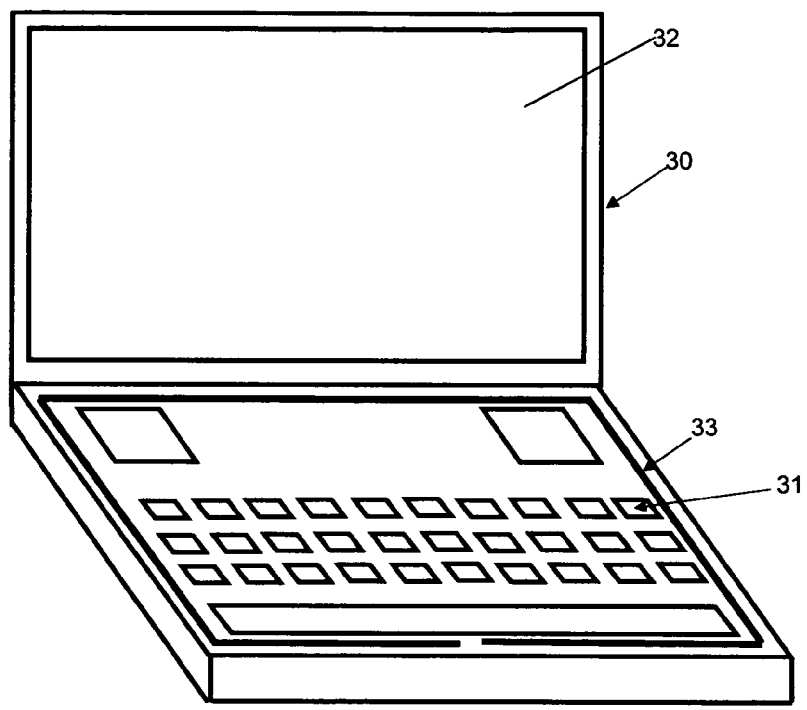
FIG. 4 is a schematic view of a device for reading the electronic version of the document of FIG. 1.

Once a document has been prepared, it can be verified by reading out the information stored in the ROM portion of the RFID chip 15 and comparing the electronic version of the information with the printed version. FIG. 4 illustrates this verification process. As seen in this FIG., a conventional lap-top computer 30 having a keyboard 31 and a display 32 is provided with a read antenna 33 at a convenient location, such as around the perimeter of the keyboard 31 as illustrated. Read antenna 33 is connected to the CPU inside computer 30 using one of the standard interfaces normally found in such computers. Computer 30 also has installed therein a computer program which is functionally capable of controlling the interrogation process using the protocols incorporated into RFID chip 15 so that the document contents in the ROM portion of RFID chip 15 can be extracted by interrogation and stored in the memory of computer 30. To extract the information, document 10 is placed on keyboard 31 and computer 30 is operated to start the interrogation process. Read antenna 33 functions to transfer power into RFID chip 15 located on document 10 and to transfer the information received via document antenna 14 into the CPU of computer 30. Once extracted, the information can be displayed on display 32 and the displayed version can be visually compared with the printed version. In addition, if desired, the displayed version can be printed out onto a sheet media blank, and this print-out can be compared with the original. As will be apparent, any variation between the original and the extracted version will prove that the original has been altered.

Figure 5:
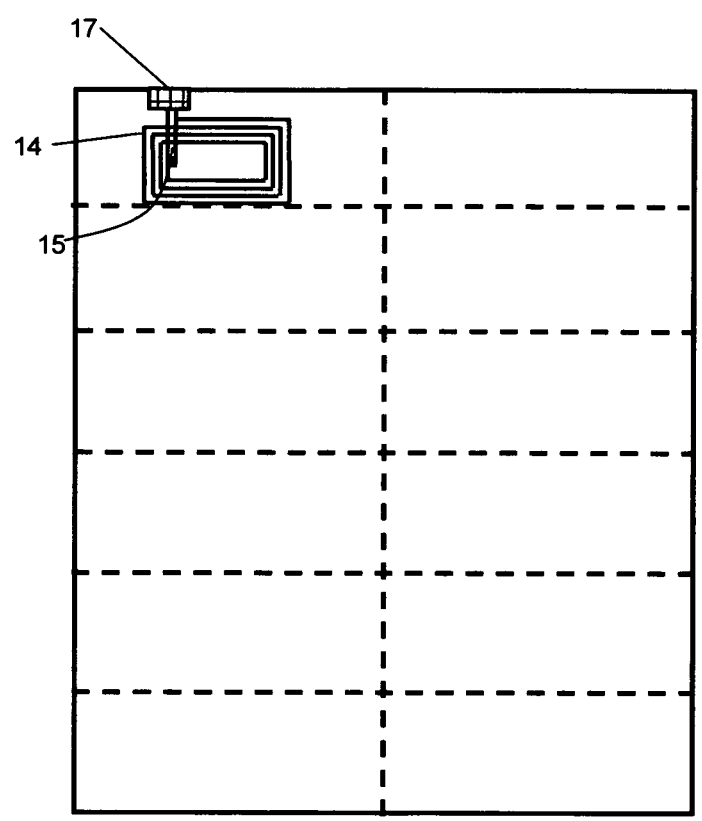
FIG. 5 is a plan view of a document illustrating an alternate embodiment of the document in which the location of the electronic components may be varied.

In order to reduce the possibility of cross-talk or other mutual interaction between the loop antennas 14 of different documents 10 when several such documents are in close proximity (as stored in a file folder or fastened together in a multi-page document), the document sheet 10 is virtually partitioned into different regions in which the ID tag for that document sheet may be located. FIG. 5 illustrates one such virtual partitioning. As seen in this FIG., a document sheet 10 is virtually partitioned into 6 rows and 2 columns. The ID tag containing antenna 14, RFID chip 15 and optional visible indicator 17 is located in row 1, column 1 for the FIG. 5 document sheet 10. For other document sheets 10, the ID tag may be located in location row 1, column 2; row 2, column 1; row 2, column 2; . . . , row 6, column 2. In general, and depending on the physical dimensions of the ID tag and sheet blanks 10, each sheet blank 10 may be virtually partitioned into m rows and n columns, where m and n are both integers. In addition, each sheet blank may have stored in the ROM portion of RFID chip 15, a character which specifies the physical location on the sheet for the ID tag. When preparing a series of sheet documents which are intended to be stored in close proximity (such as a multi-page document), the preparation process may include a routine for selecting sheet blanks having different ID tag locations for sequential document preparation. This routine may include the use of several hoppers or other containers for the sheet blanks, storing blanks with the same ID tag location in a given hopper, and feeding sheet blanks from the different hoppers in accordance with a predetermined location selection scheme.

As noted above, each sheet document 10 is optionally provided with a visible indicator 17 located near one of the margins of the sheet. Visible indicator 17 is provided in order to facilitate retrieval of a stored document. The sheet media documents, once prepared, are ultimately stored in a file folder. The file folder, in turn, is typically placed inside a file drawer. For document management purposes, the documents are typically catalogued by reference to the file folders in which they are placed. When there comes a need to physically retrieve a certain document, the standard procedure used is to consult a catalogue of documents stored in the host computer to identify the file cabinet and the file folder containing the sought document, remotely search the collection of file cabinets in the document management system to find the correct file folder, remotely search the found file folder for the document sought, go to the file cabinet, open the drawer containing the document, extract the file folder, and search through the individual documents until the sought document is found. This is very time consuming. Visual indicator 17 can shorten this process substantially. When preparing a given document, the process preferably includes the steps of generating a document identification character (a document ID character), and storing this character in the ROM portion of the RFID chip 15. A hand-held interrogator can be provided which uses the same communication protocol employed in the document preparation process described above. When the file in which the document is supposedly located is retrieved from the larger container, the hand-held interrogator can be activated to generate search signals which include the document identification character. If the sought document is in the file folder, the visible indicator incorporated therein is activated by the RFID chip 15. The searcher need only note the activated indicator 17 to retrieve the sought document. This process can also be used when searching for a document among unorganized collections of documents which are stored in large numbers loosely in a container, such as a storage box.

Figure 6:
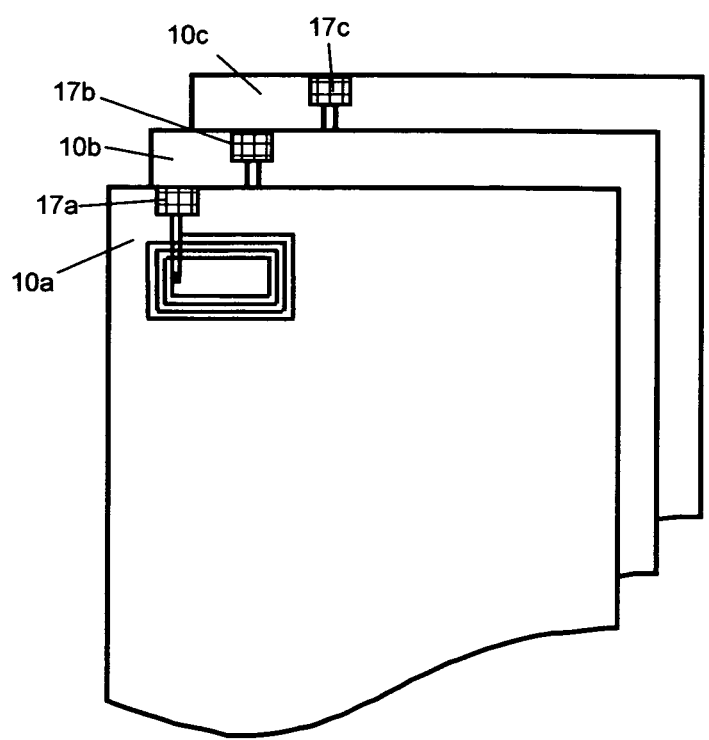
FIG. 6 is a schematic plan view of a folio of three documents illustrating an alternate embodiment in which the location of visible indicators may be varied to enhance document identification and physical retrieval.

This visual detection capability can be enhanced by staggering the locations of the visible indicators on different documents. FIG. 6 schematically illustrates three stored documents 10a, 10b, 10c each having a visible indicator 17a, 17b, 17c placed at a different lateral location on the upper margin. If such an array of documents is loosely stored in a box among many such documents, the sought document can be readily identified by the activated visible indicator 17 since the lateral spacing enhances the visibility of the activated indicator.

Preparation of documents described above is relatively straight-forward, and can be easily taught to office workers. The verification process is likewise easy to learn and to perform.

Figure 7:
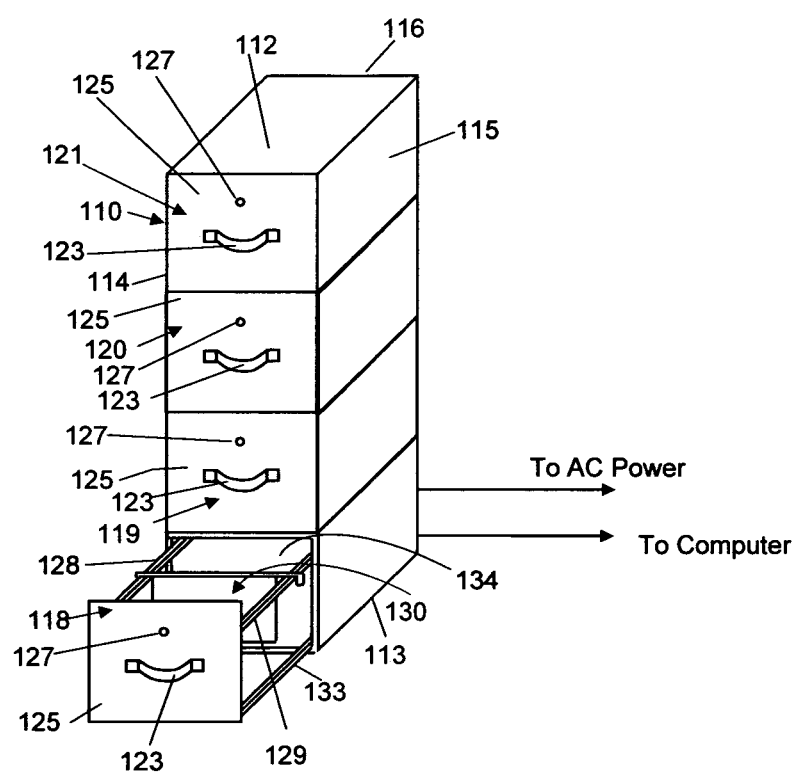
FIG. 7 is a perspective view of a multiple drawer file cabinet illustrating a first implementation of a system incorporating the invention using R.F. file folder location and R.F. document location.

FIGS. 7-14 illustrate a multiple drawer file cabinet with a first implementation of a system incorporating the invention using R.F. file folder location and R.F. document location. FIG. 7 is a perspective view, taken from the right front, of a file cabinet in a system using direct electrical connections between individual file cabinets and the associated host computer. As seen in this FIG., a multiple drawer file cabinet 110 (four drawers illustrated) of known mechanical construction has the usual top 112, bottom 113, sides 114, 115, and back 116. Four drawers 118-121 are slidably mounted in cabinet 110, each drawer 118-121 having a drawer pull 123 mounted on a front panel 125 thereof. A visible indicator device 127 is also mounted on the front panel 125 of each drawer 118-121. Indicator 127 may comprise any one of a number of known elements capable of providing a visible signal when activated in the manner described below. Examples of suitable indicators are a conventional LED indicator, and a type 276-036 flashing LED indicator available from Radio Shack Corporation.

Lowermost drawer 118 is shown in the opened position in order to provide a perspective view of the basic drawer structure and the manner in which a file folder is removably supported in a file drawer. As shown, drawer 118 is provided with a pair of upper support rails 128, 129, which serve the primary purpose of supporting individual file folders, such as file folder 130, in the drawer. Secondarily, rails 128, 129 may also provide structural rigidity for the drawer 118 itself. Drawer 118 also has a pair of lower rails 132, 133 (only one of which is visible in FIG. 7) which complete the horizontal structural elements. In a commonly used file cabinet structure, rails 128, 129, 132, and 133 may form an inner frame insert (along with vertically arranged frame members) which can be physically installed in a standard drawer. To complete the drawer structure, a back 134 is connected to the rails 128, 129, 132, 133. All file folders, such as folder 130, are removably supported by upper rails 128, 129 using horizontal support braces (described below) to which the folder 130 is mechanically secured. The mechanical structure of folder 130 and rails 128, 129 is conventional. The structure and arrangement of drawers 119-121 are identical to that of drawer 118. As indicated by the legended lead lines shown to the lower right of file cabinet 110, an A.C. power connection provides A.C. electrical power to the electronic components described below and located within file cabinet 110. Similarly, a hard-wired connection is coupled between file cabinet 110 and an associated system computer for the purposes described below.

Figure 8:
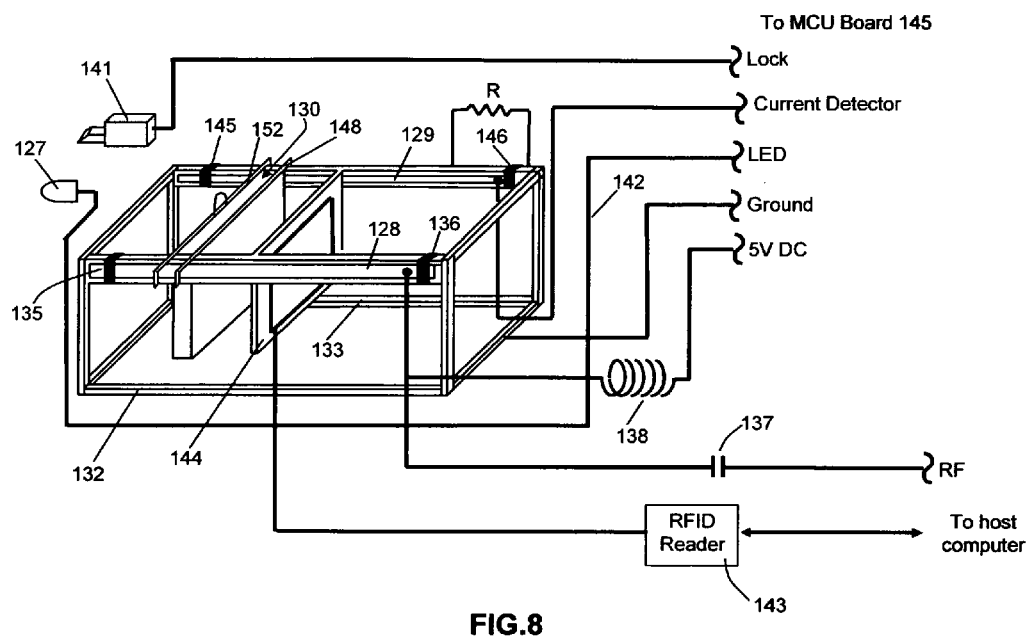
FIG. 8 is a schematic side perspective view of a single file drawer and file folder.

As best shown in FIG. 8, upper support rail 128 of each drawer 118-121 is electrically isolated from the remaining drawer frame structure by means of insulating elements 135, 136, and is electrically connected to a local R.F. source (described below) via a capacitor 137, which passes R.F. signals to upper rail 128 but blocks D.C. electrical signals. In addition, upper rail 128 is electrically connected to a local source of D.C. power (described below) via a choke coil 138, which passes D.C. power to upper rail 128 but blocks R.F. signals which might be present. Upper support rail 129 of each drawer 118-121 is electrically isolated from the remaining drawer frame structure by means of insulating elements 145, 146, and is electrically coupled to a drawer current detector 139 shown in FIG. 14, which is positioned in a convenient location in the associated drawer and which detects the passage of D.C. current through a file folder circuit described below. The drawer indicator 127, and an electromechanical drawer lock 141 are electrically connected to an associated microcomputer shown in FIG. 9, along with a ground connection 142.

An RFID reader 143 is coupled to an RFID reader antenna 144 positioned substantially mid-way between the front and rear of drawer 118. RFID reader 143 may comprises any one of a number of known RFID readers, such as a type DLP-RFID1 RFID reader available from DLP Design, Inc. of Allen, Tex.; or a type MARS-24 RFID reader available from Magellan Technology Pty Ltd of Sydney, Australia. Preferably RFID reader 143 is a single unit with multiple antenna compatability so that only a single RFID reader need be installed in a given cabinet 110. RFID reader 143 is coupled to a system host computer and is controlled by document identifier signals received directly from the system host computer. RFID reader 143 functions to interrogate individual documents 10 located in file folders 130 in a given file cabinet drawer, such as drawer 118.

Figure 9:
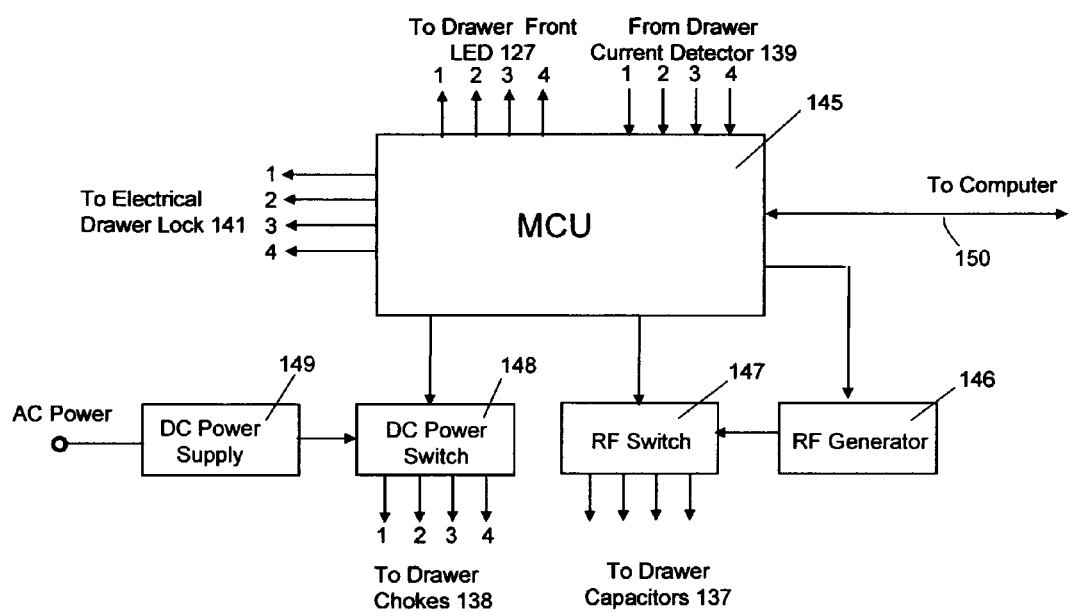
FIG. 9 is a block diagram of an electronic cabinet system located in each file cabinet.

Within each file cabinet 110 is a cabinet system shown in FIG. 9. As seen in this FIG., a microcomputer unit 145, preferably a type AT89C2051 unit available from Intel Corporation, has a plurality (four in the implementation shown) of inputs from the individual drawer current detectors 140 in the associated file cabinet 110. Microcomputer unit 145 supervises and controls the operation of an R.F. generator 146, an R.F. switch 147, and a D.C. power switch 148. R.F. generator 146 is a conventional unit capable of generating an R.F. signal of a specific frequency over a frequency range of interest (e.g., 2-20 mHz) in response to control signals from microcomputer unit 145. R.F. switch 147 is a conventional unit capable of routing R.F. signals from R.F. generator 146 to individual ones of the capacitors 137 connected to the upper rails 128 in the individual drawers of file cabinet 110, as specified by control signals from microcomputer 145. D.C. power switch 148 is a conventional unit capable of supplying D.C. power derived by a D.C. power supply 149 from the A.C. power input supplied to file cabinet 110 to individual ones of the choke coils 138 connected to the upper rails 128 in the individual drawers of file cabinet 110, as specified by control signals from microcomputer unit 145. Microcomputer unit 145 has a plurality (four in the implementation shown) of control signal outputs used to activate the drawer front LEDs of file cabinet 110. Microcomputer unit 145 has another plurality (four in the implementation shown) of control signal outputs used to activate the electrical drawer locks 141 of the individual drawers 118-121 of file cabinet 110.

Microcomputer unit 145 receives information signals from the associated system host computer via communication cable 150. These information signals include an identification of a given file folder being requested.

As seen in FIG. 8, each file folder 130 has the conventional U-shaped cross-sectional construction which has proven to be popular in the office equipment industry for containing documents. Each side (front and back) of folder 130 is mechanically supported by a mechanical brace. One of the braces (brace 148) is of unitary construction and comprises a single rigid electrically non-conductive arm having downwardly folded hook-like ends which slidably engage the support rails 128, 129. The other brace (brace 152) has a special construction according to the invention.

Figure 10:
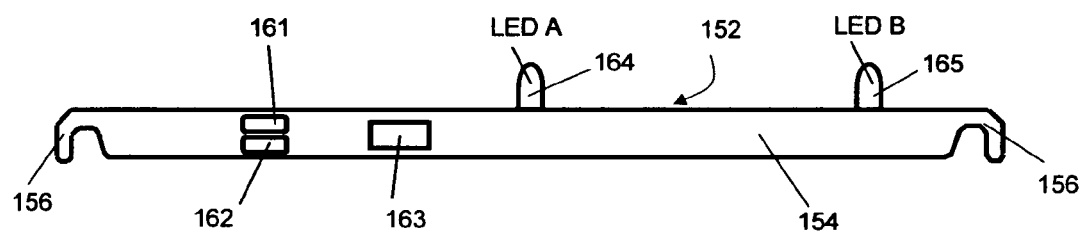
FIG. 10 is a front elevational view of a folder brace bearing the electrical components located at the file folder.

With reference to FIG. 10, which is a front elevational view of brace 152, this element includes a main electrically non-conductive support member 154 with a downwardly turned hook-like end 156 at each end which mechanically engages the associated one of rails 128, 129 when the folder is properly positioned in the file drawer. Brace 152 is preferably fabricated from a printed circuit board material on which electrically conductive circuit patterns may be formed and on which circuit components may be mounted. An R.F. responsive electrical circuit comprising a pair of crystals 161, 162, an integrated circuit 163, and a pair of LED indicators 164 (LED A) and 165 (LED B) is mounted on brace 152. The electrical circuit comprising crystals 161,162, integrated circuit 163, and LED indicators 164, 165 is electrically connected between hook ends 156 of brace 152 preferably by providing conductive paths on brace 152 between the appropriate circuit nodes and the surfaces of hook ends 156 which confront the surfaces of rails 128, 129 when a folder 130 is suspended by the rails 128, 129. LEDs 164, 165 are mechanically supported by brace 152 in such a manner as to protrude above the upper margin of file folder 130 so that both LEDs are visible above the file folder when the file drawer 118 is opened.

Figure 11:
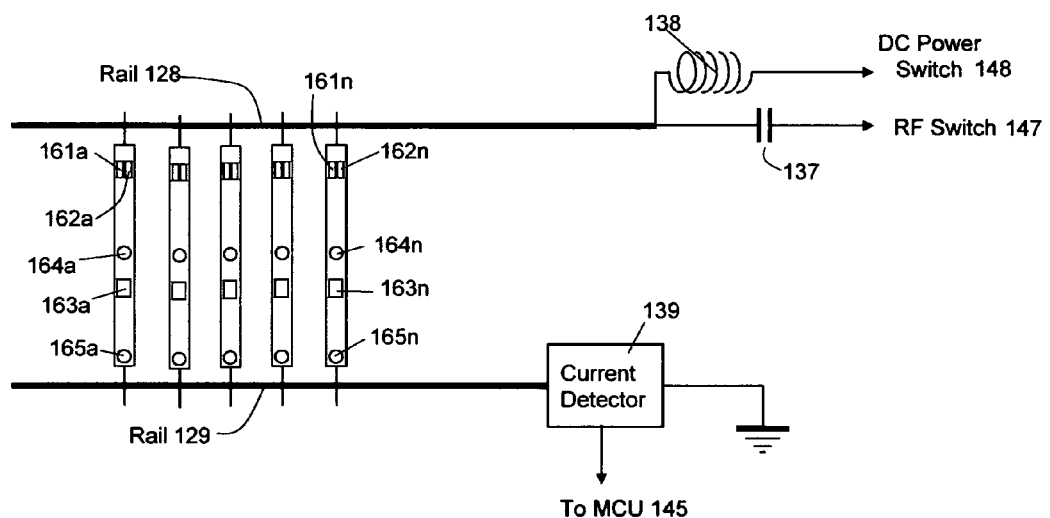
FIG. 11 a schematic top view showing the manner in which a plurality of folder circuits can be physically arranged in a single file drawer of a file cabinet.

FIG. 11 is a schematic top view showing the manner in which a plurality of file folder circuits can be physically arranged in a single file drawer. As seen in this FIG., each folder circuit 161*i*-165*i* is electrically coupled across conductive support rails 128, 129 with all circuits connected in parallel. Current detector circuit 139 has a first node coupled to rail 129 and a second node coupled to microcomputer unit 145 of FIG. 9. Choke coil 138 is coupled between rail 128 and the associated one of the power output terminals of D.C. power switch 148. Capacitor 137 is coupled between rail 128 and the associated one of the R.F. output terminals of R.F. switch 147.

Figure 12:
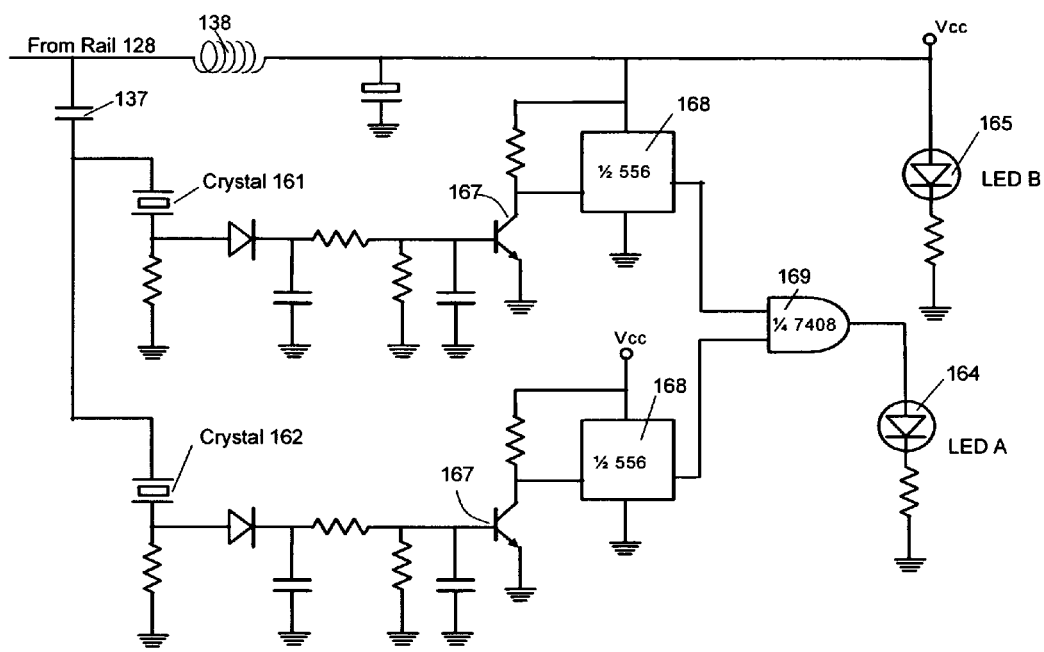
FIG. 12 is a schematic diagram of the folder circuit incorporated into the folder brace 52 of each file folder.

FIG. 12 is a schematic diagram of the file folder circuit incorporated into the folder brace 152 of each folder. As seen in this FIG., each file folder circuit includes a pair of crystals 161, 162 coupled in parallel via capacitor 137 to rail 128 of the associated drawer. Each pair of crystals 161, 162 in a given file folder circuit has a combined pair of resonant frequencies different from that of the paired crystals in the other file folder circuits. All resonant frequencies are preferably in the R.F. range of the spectrum, and may range in value from about 2 mHz. to about 20 mHz. The frequency separation between crystals is a matter of design choice, and good results have been obtained with crystals in the 2 mHz-20 mHz range by using a minimum frequency separation of 0.001 MHz. When R.F. signals are present on rail 128, they pass through capacitor 137 and are presented in parallel to crystals 161, 162. If the R.F. signals match the frequency of either (or both) of crystals 161, 162, the crystal whose frequency is matched will resonate and present a low resistance to the passage of R.F. current therethrough. This current will switch a transistor 167, which will activate a one-shot circuit 168. If both one-shot circuits 168 are active, their combined outputs will enable an AND gate 169, which in turn will illuminate LED 164 to indicate that the folder has been identified. At the same time, the current detector 139 for the drawer in which the folder is located will illuminate the drawer panel LED 127 in the manner described below.

Figure 13:
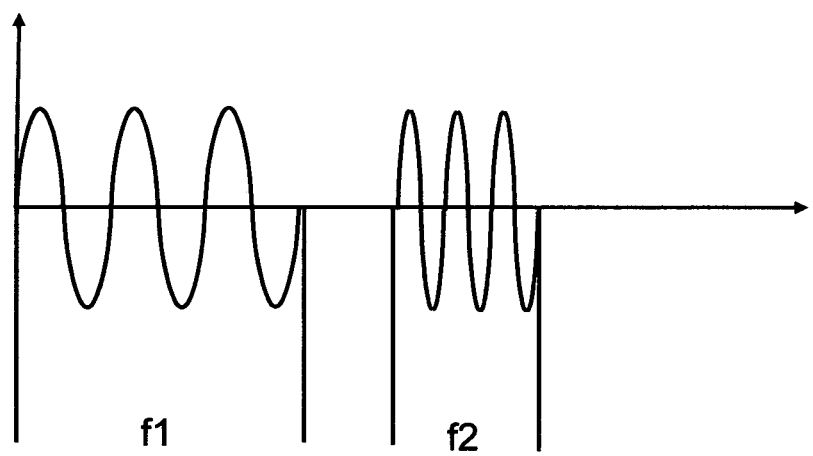
FIG. 13 is an R.F. waveform diagram illustrating the R.F. output signals from a cabinet R.F. generator over one system cycle.

In order to comply with broadcast radiation power constraints imposed by governmental agencies, and to minimize the power requirements of the R.F. generators 146 housed in each file cabinet 110, the preferred technique for generating the R.F. signals is to alternately generate the R.F. signals at the resonant frequencies of the two crystals 161, 162. This is illustrated in FIG. 13. As seen in this FIG., which illustrates the R.F. output signals from an R.F. generator 146 over one system cycle, the R.F. generator first generates an R.F. signal of frequency f1 for a number of cycles, terminates that signal for a brief period of time, then generates an R.F. signal of frequency f2 for a number of cycles, and then terminates that signal for a brief period of time. This cyclical operation is repeated for a sufficient length of time to ensure that the operator has sufficient time to locate the correct file cabinet and drawer (by observing the illuminated drawer LED 127 and file folder LED 164). LED 164 of the correct folder circuit will remain illuminated so long as there exists an overlap between the processed R.F. signals passing through crystals 161, 162. Drawer LED 127 will remain illuminated so long as current is passing through one of the file folder circuits caused by resonance of the crystals 61, 62.

Figure 14:
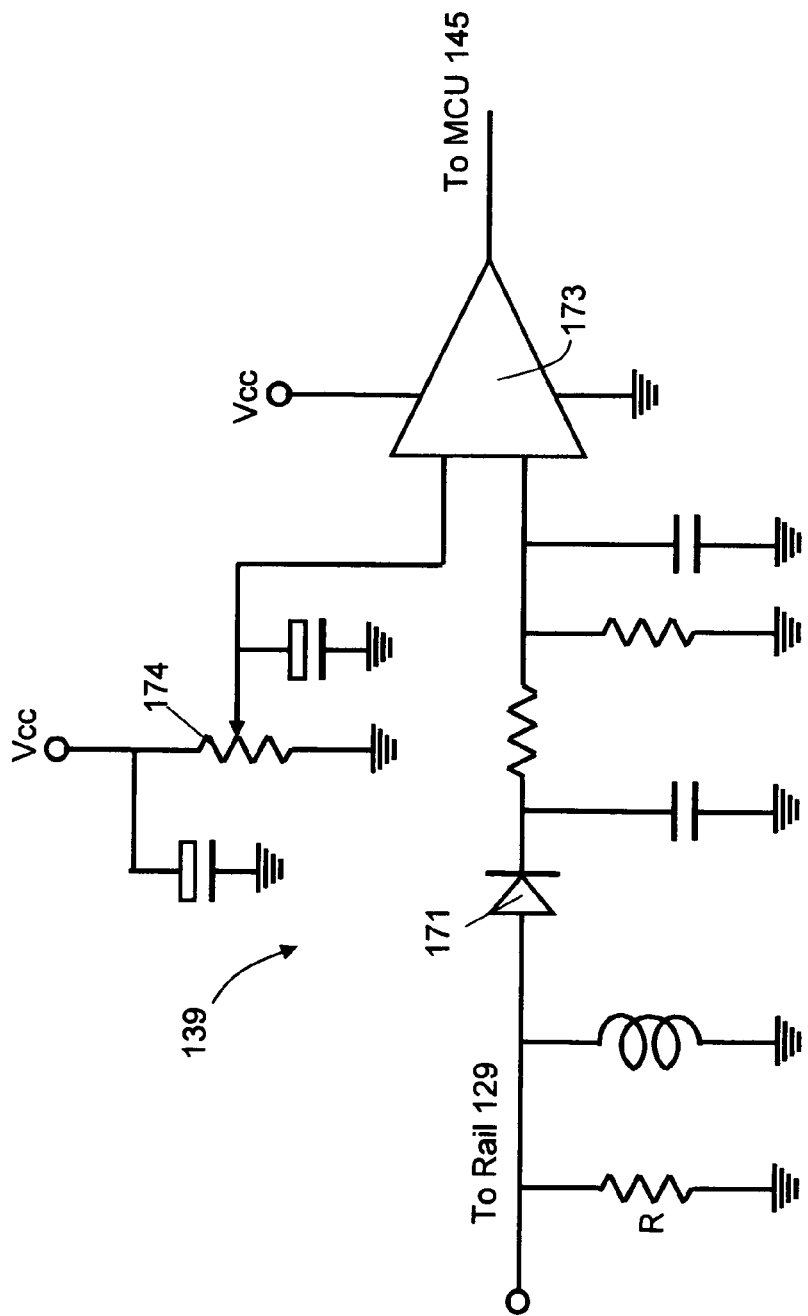
FIG. 14 is a schematic diagram of a current detector for each drawer in a file cabinet.

FIG. 14 is a schematic diagram of current detector 139 for each drawer in a file cabinet 110. As seen in this FIG., D.C. current flowing along rail 129 is coupled via a diode 171 and a filter network to a first reference input of an operational amplifier 173. A reference threshold D.C. value is supplied to the other reference input of operational amplifier 173. The value of the D.C. reference voltage can be adjusted by varying the resistance of a variable resistance element 174. So long as one of the folder circuits is active (i.e., the crystals 161, 162 are in resonance), there will be sufficient current present on rail 129 to generate an active signal at the output of operational amplifier 173. This signal is coupled to microcomputer unit 145, which in response generates enabling signals to illuminate the correct drawer front LED 127 and to activate the correct drawer lock 141.

To retrieve a specific document from a file folder in the system, the operator enters the document sought information into the system host computer, which contains a complete list of documents, file folders and the file cabinet in which each folder is located. The system host computer initially transmits a file folder request to the microcomputer unit 145 in the correct file cabinet 110 in order to locate the file folder in which the sought document is located according to the system records, and the corresponding microcomputer unit 145 activates the file cabinet R.F. signal generator 146 and R.F. switch 147 to supply R.F. signals of the appropriate R.F. frequency pair to the drawer in which the sought file folder should be located, along with D.C. power. If the sought file folder is actually located in the proper drawer, the microcomputer unit 145 receives a feedback signal from the drawer current detector 139 and generates an operating signal for the drawer front LED 127 and the drawer lock 141. Should an operator open the drawer having the illuminated drawer front LED 127, the correct file folder would be indicated by the illuminated file folder LED 164.

Once a file folder has been found by the file folder location system elements, the local microcomputer 145 transmits this event to the system host computer. In response, the system host computer generates document identifier signals and transmits these signals to the RFID reader 143 located in the file cabinet 110 containing the found file folder 130. RFID reader 143 generates an R.F. document tag interrogation signal, which is transmitted by RFID reader antenna 144 to all documents within the drawer containing the found file folder 130. If the document corresponding to the document identifier signals is present in any of the file folders contained in the drawer, the RFID tag associated to that document will respond to the interrogation signal from RFID reader 143 according to the RFID protocol implemented. For example, the tag can respond by transmitting a signal containing the tag identification information, followed by the contents of that document. When RFID reader 143 receives this information via RFID reader antenna 144, it relays this information to the system host computer for further use. If no response is received by RFID reader 143 within a preselected period of time, RFID reader 143 may repeat the transmission to the RFID reader antenna 144, or transmit a document not found signal back to the system host computer, depending on the system protocol established.

The R.F. signal generator in each file cabinet 110 may comprise a sweep frequency generator capable of generating paired R.F. signals in a swept mode, beginning with the first crystal resonant frequency pair in the document management system, and ending with the last crystal resonant frequency pair in the system. With such a signal generator, the integrity of the entire collection of file folders can be quickly checked by instructing the microcomputer unit 145 in each file cabinet 110 to activate the R.F. signal generator in the sweep mode. As the paired signal frequencies are swept over the entire range, all file folder circuits which are present in a given file cabinet 110 will resonate at their respective frequencies and this can be detected by the microcomputer unit 145 in each file cabinet 110 using a conventional R.F. detector circuit. Any missing file folder will not respond, and this also can be detected by the microcomputer unit 145 in each file cabinet 110 using the same circuit. Any file folder detected as missing can be reported by a given microcomputer unit 145 in each file cabinet 110 to the system host computer and correlated by the system host computer to the file folder identification in the computer by noting the frequencies of the non-responsive folder circuits.

Similarly, the integrity of the entire collection of documents in the system can be checked by operating the system host computer to generate sequentially the document identifier signals for all documents registered in the system. The host computer initially sends each document identifier signal to the RFID reader 143 in the file cabinet 110 in which the document corresponding to the document identifier signal supposedly resides (according to the system master list). The RFID reader 143 in that file cabinet 110 then generates an interrogation signal and waits for a response. If a response is received, this event is transmitted by the RFID reader 143 back to the system host computer as a document found signal. If no response to the interrogation signal is received, this event is transmitted by the RFID reader 143 back to the system host computer as a document not found signal. The system host computer may proceed at that point to re-send the same document identifier signal to the RFID reader 143 in the same file cabinet 110 with an instruction to transmit a document interrogation signal to the documents in a different drawer of that file cabinet 110. If a document found signal results, the system host computer will update the system records to note the new drawer location of the document. If no document found signal results from the interrogation of all documents in all drawers of the originally selected cabinet 110, the system host computer may proceed at that point to sequentially send the same document identifier signal to all file cabinets 110 in the system and wait for responses from the RFID readers 143 in the other file cabinets. If no document found response is received, the system host computer can then add that document to a missing documents list. If a document found response is received from one of the cabinets 110 in the system, the system host computer can update the master list of documents to note the new location of the document.

The system may be initially configured for the file folders in several different ways. The most fundamental way is to place a single file folder 130 into a drawer in a file cabinet 110, cause the cabinet R.F. signal generator 146 to sweep the range of paired frequencies, note the frequencies at which the crystals in that folder resonate, enter those frequency numbers into a list in the microcomputer unit 145 memory, remove the folder, insert another folder, and repeat this process for all folders desired on a serial basis. Once all file folders have been processed, appropriate file folder identification information is transmitted from microcomputer unit 145 of a given file cabinet 110 to the system host computer. This method works well for a new system with no existing file folders and a relatively small number of file folders required initially. A more useful technique is to insert a first file folder into a drawer, sweep the permitted R.F. frequency pairs, note the resonant frequencies, enter those numbers into a new list; insert a second file folder to the drawer without removing the first, sweep the frequency pairs, add the resonant frequencies of the new file folder to the list; insert a third file folder into the drawer, sweep the frequency pairs, add the resonant frequencies of the third folder to the list; etc. As each new file folder is inserted into the drawer, the microcomputer unit 145 has a running list of frequencies already identified and, since each pair of crystal frequencies is unique, there can be no duplications.

To register documents in the system, the RFID tag number of a given document is entered into the system master list, either manually by means of a keyboard coupled to the system host computer or by using a tag reader coupled to the system host computer. Along with the RFID tag number, a description of the document contents and an identification of the file folder in which the document is to reside are entered by an operator into the system master list. As new documents are added, this process is carried out for the new document information so that, at any given time the system master list contains a complete catalog of all documents and file folders in the system, along with the file cabinet and drawer location of each file folder.

Figure 15:
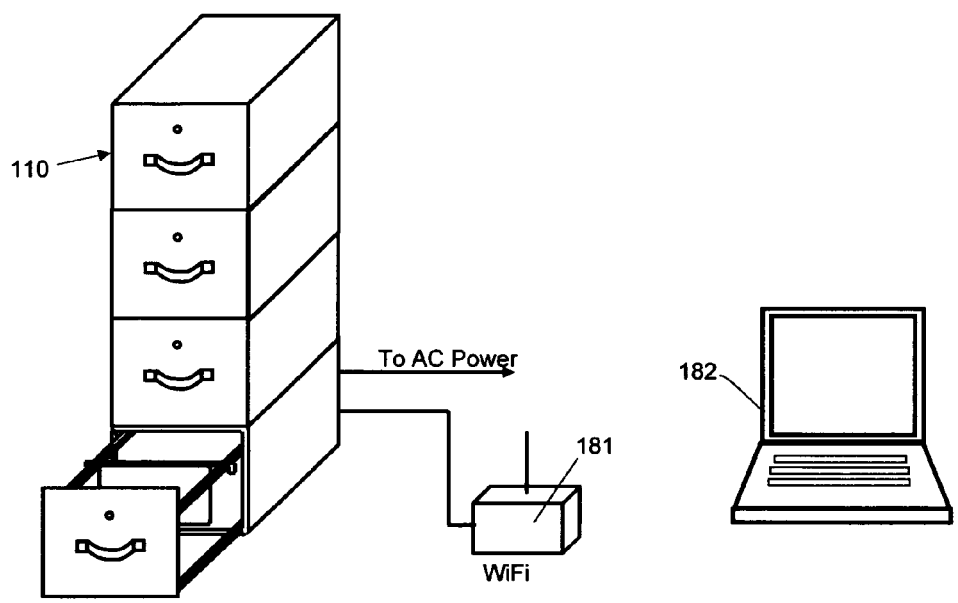
FIG. 15 is a perspective view of a multiple drawer file cabinet in a wireless documents management system implementation of the invention using wireless communication between the individual file cabinets and the associated computer.

FIG. 15 illustrates an alternate embodiment of the documents management system implementation of the invention using wireless communication between the individual file cabinets and the associated computer. As seen in this FIG., each cabinet 110 is provided with a transceiver 181 for communication with the system host computer 182. The system host computer 182 is provided with a matching internal transceiver. Operation of the FIG. 15 system is essentially identical to that of the FIG. 1 system, with the exception that the folder identification signals and document identifier signals are transmitted to file cabinet 110 using wireless transmission, rather that the hard wired connections of the FIG. 1 embodiment. In addition, there may be additional security considerations to the wireless embodiment of FIG. 15 to prevent unauthorized transmission and reception of the R.F. signals.

Figure 16:
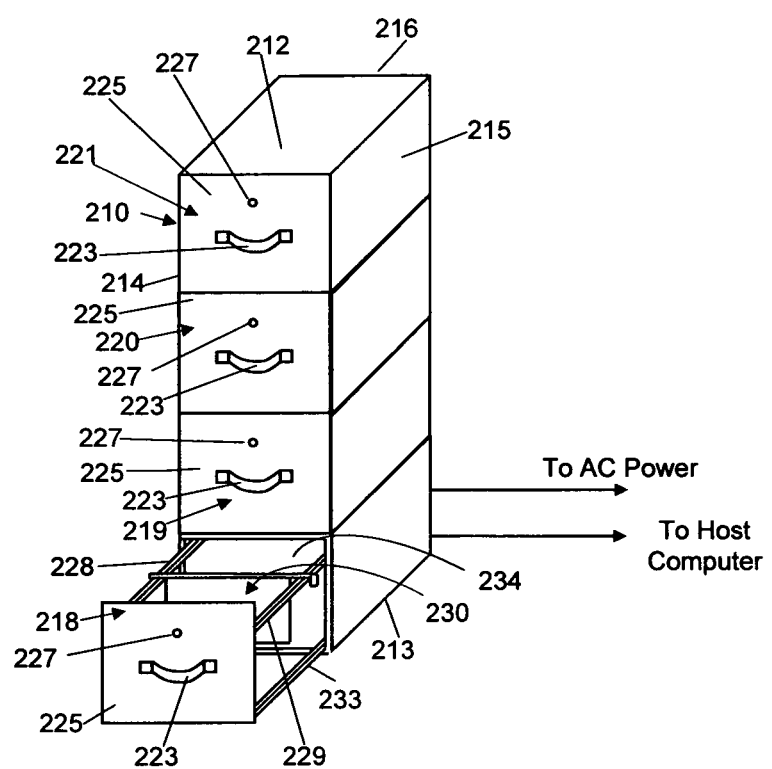
FIG. 16 is a perspective view of a multiple drawer file cabinet illustrating a second implementation of a system incorporating the invention using file folder location with addressable decoder units and R.F. document location.

FIGS. 16-22 illustrate a multiple drawer file cabinet with a second implementation of a system incorporating the invention using addressable decoder file folder location and R.F. document location. FIG. 16 is a perspective view, taken from the right front, of a file cabinet in a system using direct electrical connections between individual file cabinets and the system host computer. As seen in this FIG., a multiple drawer file cabinet 210 (four drawers illustrated) of known mechanical construction has the usual top 212, bottom 213, sides 214, 215, and back 216. Four drawers 218-221 are slidably mounted in cabinet 210, each drawer 218-221 having a drawer pull 223 mounted on a front panel 225 thereof. A visible indicator device 227 is also mounted on the front panel 225 of each drawer 218-221. Indicator 227 may comprise any one of a number of known elements capable of providing a visible signal when activated in the manner described below. Examples of suitable indicators are a conventional LED indicator, and a type 276-036 flashing LED indicator available from Radio Shack Corporation.

Lower-most drawer 218 is shown in the opened position in order to provide a perspective view of the basic drawer structure and the manner in which a file folder is removably supported in a file drawer. As shown, drawer 218 is provided with a pair of upper support members 228, 229 described in detail below, which serve the primary purpose of supporting individual file folders, such as file folder 230, in the drawer. Secondarily, support members 228, 229 may also provide structural rigidity for the drawer 218 itself. Drawer 218 also has a pair of lower members 232, 233 (only one of which (member 233) is visible in FIG. 16) which complete the horizontal structural elements. In a commonly used file cabinet structure, members 228, 229, 232, and 233 may form an inner frame insert (along with vertically arranged frame members) which can be physically installed in a standard drawer. To complete the drawer structure, a back 234 is connected to the members 228, 229, 232, 233. All file folders, such as folder 230, are removably supported by upper support members 228, 229 using horizontal support braces (described below) to which the folder 230 is mechanically secured. The mechanical structure of folder 230 is conventional. The structure and arrangement of drawers 219-221 are identical to that of drawer 218. As indicated by the legended lead lines shown to the lower right of file cabinet 210, an A.C. power connection provides A.C. electrical power to the electronic components described below and located within file cabinet 210. Similarly, a hard-wired connection is coupled between file cabinet 210 and an associated host computer for the purposes described below.

Figure 17:
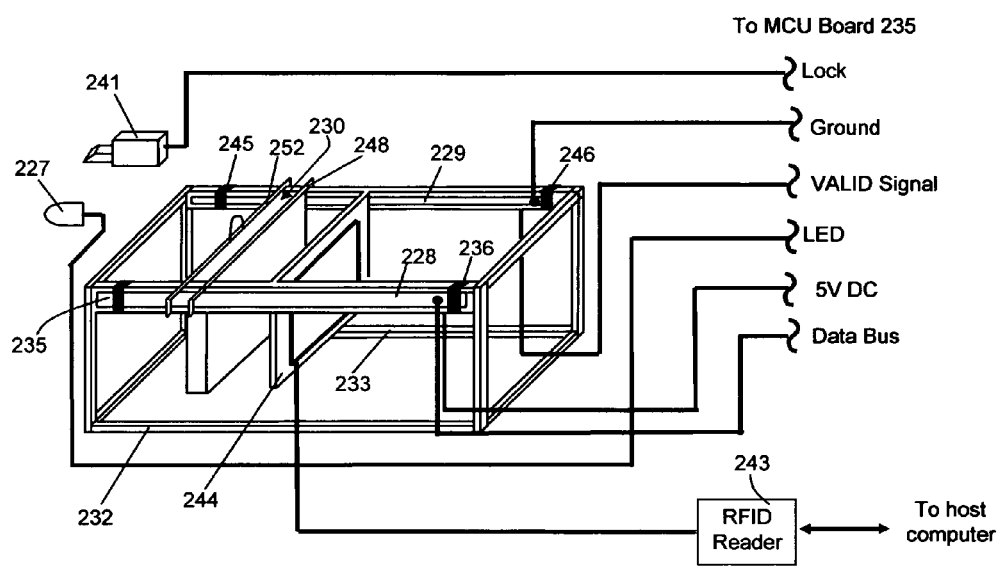
FIG. 17 is a schematic side perspective view of a single file drawer and file folder and associated elements according to the invention.

As best shown in FIG. 17, each folder, such as folder 230 depicted in this FIG., is mechanically supported in a removable manner by upper support members 228, 229. Upper support members 228, 229 of each drawer 218-221 are electrically isolated from the remaining drawer frame structure by means of insulating elements described below. Also, upper support members 228, 229 are each provided with two electrically conductive strips which are connected by individual conductors to four terminals of a local microcomputer 235 located in the filing cabinet 210. These four terminals are labeled "Data Bus", "+5V", "Ground", and "VALID Signal" in FIG. 17. Microcomputer 235, which is preferably a type AT89C2051 device available from Intel Corporation of Santa Clara, Calif., is coupled to a host computer (not illustrated in FIG. 17) and also to a suitable source of D.C. power (+5V) derived from the A.C. power input noted above. Microcomputer 235 has a pair of output terminals labelled "LED" and "Lock" for controlling the state of indicator 227 and an electrically operated drawer lock mechanism 237. The "+5V" and "Ground" terminals provide D.C. power to the circuitry located in each file folder located in a drawer. The "Data Bus" terminal supplies address information to the file folder circuitry. The "VALID Signal" terminal receives a VALID signal whenever the file folder circuitry of a given file folder decodes an address received from microcomputer 235 which matches the address of that file folder circuitry.

An RFID reader 243 is coupled to an RFID reader antenna 244 positioned substantially mid-way between the front and rear of drawer 218. RFID reader 243 may comprises any one of a number of known RFID readers, such as a type DLP-RFID1 RFID reader available from DLP Design, Inc. of Allen, Tex.; or a type MARS-24 RFID reader available from Magellan Technology Pty Ltd of Sydney, Australia. Preferably RFID reader 243 is a single unit with multiple antenna capability so that only a single RFID reader need be installed in a given cabinet 210. RFID reader 243 is coupled to a system host computer and is controlled by signals received directly from the system host computer. RFID reader 243 functions to interrogate individual documents 10 located in file folders 230 in a given file cabinet drawer, such as drawer 218.

Figure 18:
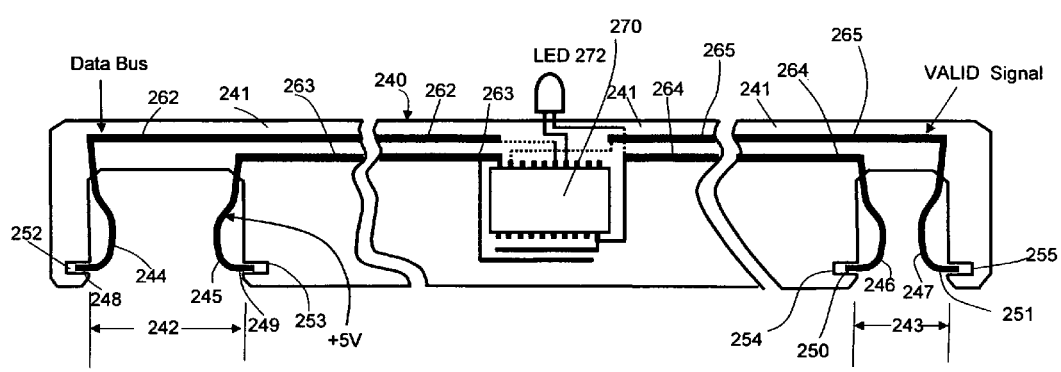
FIG. 18 is a front elevational view partially broken away of a folder brace bearing the electrical components located at the file folder according to the invention.
Figure 19:
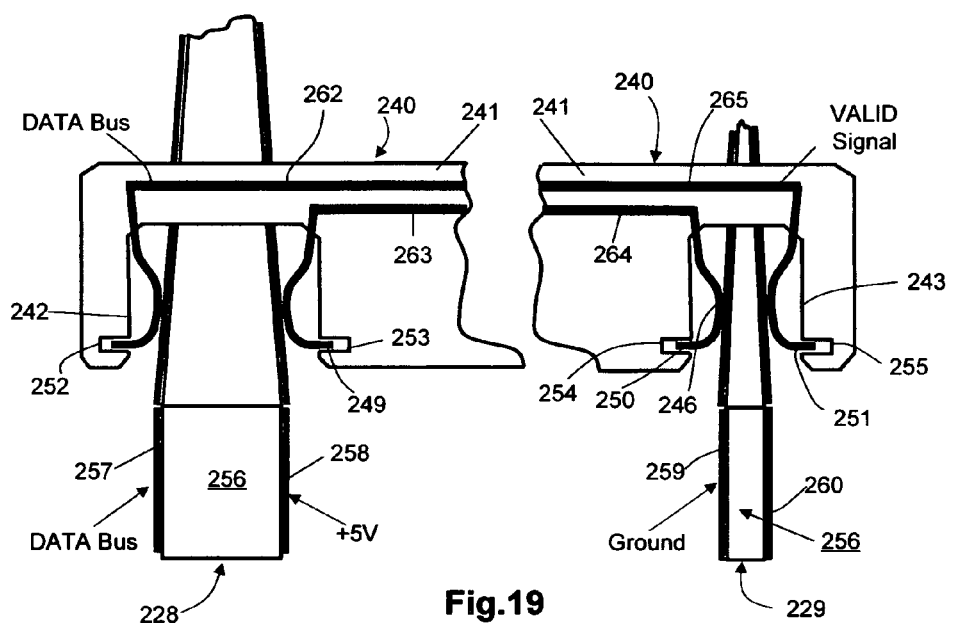
FIG. 19 is a fragmentary view of a single folder brace and a pair of upper support members for the folder brace showing the manner in which the folder brace is removably attached to the upper support members according to the invention.

FIGS. 18 and 19 illustrate the structure of the primary one of the two horizontal support braces incorporated into each file folder 230. The other horizontal brace for each folder is of conventional electrically-nonconductive construction. As seen in these Figs., the primary support brace 240 has an elongate body structure 241 formed from a suitable electrically non-conductive material, such as conventional circuit board material, phenolic, or the like. At each end, the elongate body structure has a cut-out channel 242, 243 having a width slightly larger than the width of the corresponding upper support member 228, 229. Each cut-out channel 242, 243 is provided with a pair of spring contacts 244-247 which are secured to the elongate body structure in any suitable manner, such as by heat stamping, gluing, or mechanically embedding. Each spring contact has a free end 248-251 which is received in a corresponding slot 252-255 formed in elongate body structure 241. The separation distance between the proximate portions of spring contacts 244-245, and 246-247 is slightly less than the width of the corresponding upper support member 228, 229 so that effective mechanical and electrical contact will be made when a primary brace is installed on upper support members 228, 229.

To facilitate correct installation of a primary brace, the widths of cut-out channels 242, 243 and the separation distances between spring contacts 244, 245 and 246, 247 are substantially different so that a primary brace can only be installed in one orientation. This is necessary in order to ensure that the proper electrical connections are made whenever a primary brace in installed in a file drawer.

Correspondingly, the widths of upper support members 228, 229 are different as best depicted in FIG. 19. As seen in this FIG., each upper support member 228, 229 has a central core 256 fabricated of electrically non-conductive material, such as the same material used for the fabrication of elongate body structure 241; and a pair of electrically conductive strips 257-260 secured to the outer side surfaces and extending along the length of upper support members 228, 229. Each electrically conductive strip 257-260 is dedicated to a different electrical signal, with strip 257 electrically connected to the Data Bus terminal of microcomputer 235, strip 258 electrically connected to the +5V terminal of microcomputer 235, strip 259 connected to the Ground terminal of microcomputer 235, and strip 260 electrically connected to the VALID Signal terminal of microcomputer 235.

With reference to FIG. 18, each spring contact 244-247 is electrically connected to a separate electrically conductive path 262-265, each of which is electrically connected to a different terminal of a decoder integrated circuit chip 270. Decoder chip 270 is a commercially available device which receives multi-bit address information along Data Bus conductor 262 from microcomputer 235, compares this address information with a unique address stored in decoder chip 270, generates a VALID Signal when the received address matches the stored address, and activates a folder LED 272 mounted on the upper margin of elongate body structure 241 of folder 230 in a position so as to be visible when the drawer is open. The internally generated activation signal for folder LED 272 is latched by the decoder so that, once an address match is detected, the folder LED 272 activation signal remains active until the decoder 270 latch is reset by removing the folder from the upper support members 228, 229, or D.C. power is otherwise removed. The VALID signal remains asserted so long as the received address matches the stored address and is used by microcomputer 235 to activate the drawer lock mechanism 237 and the drawer indicator 227. Decoder chip 270 is preferably a type PT2272 decoder available from Princeton Technology Corp. of Taipei, Taiwan.

Figure 20:
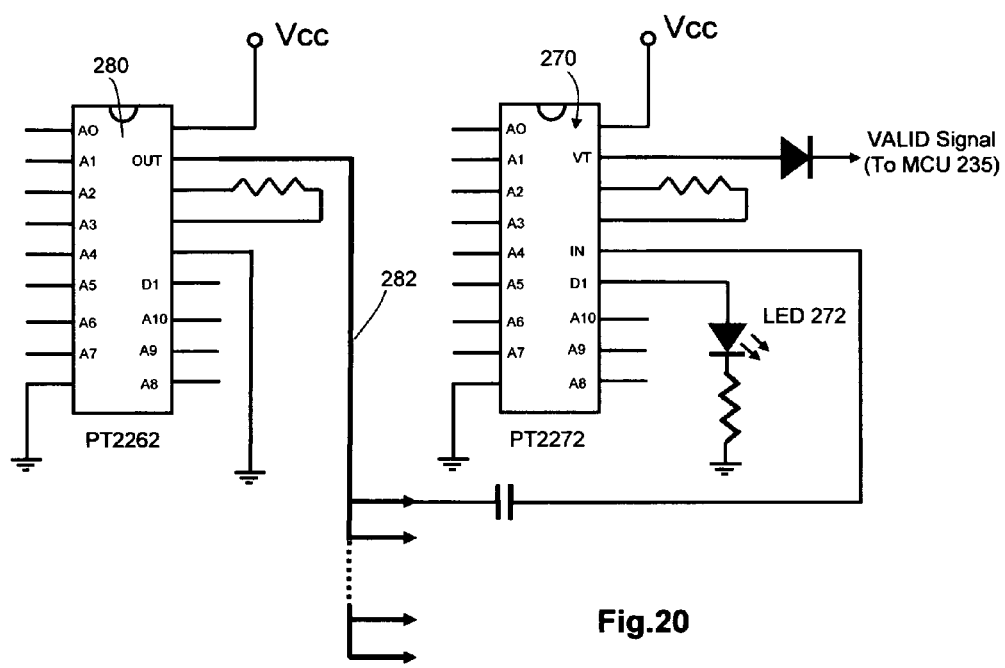
FIG. 20 is a schematic diagram of an encoder and decoder used to encode and decode the object addresses according to the invention.

FIG. 20 is a schematic diagram illustrating a single decoder 270 and a matching encoder 280. Encoder 280 is preferably a type PT2262 encoder available from Princeton Technology Corp. of Taipei, Taiwan. Encoder 280 has a plurality of address input terminals A0-A10 to which address input signals are supplied by a host computer (not illustrated in FIG. 20). An output terminal labeled "OUT" serially outputs the address information supplied to address input terminals A0-A10. These address output information signals are transmitted via conductor 282 to the address input IN of decoder 270. Decoder 270 has a plurality of address input terminals A0-A10 which are hard-wired to a unique address. In the preferred implementation, decoder 270 is a tri-state device such that the hard wire connections to address inputs A0-A1—can be either ground, Vcc or floating. The address signals generated by encoder 280 are AC coupled to the address IN terminal of decoder 270. When received, the address signals from encoder 280 are compared internally of decoder 270 with the hard-wired decoder address signals. If a match occurs, folder LED 272 is activated and a VALID Signal is generated by decoder 270.

Figure 21:
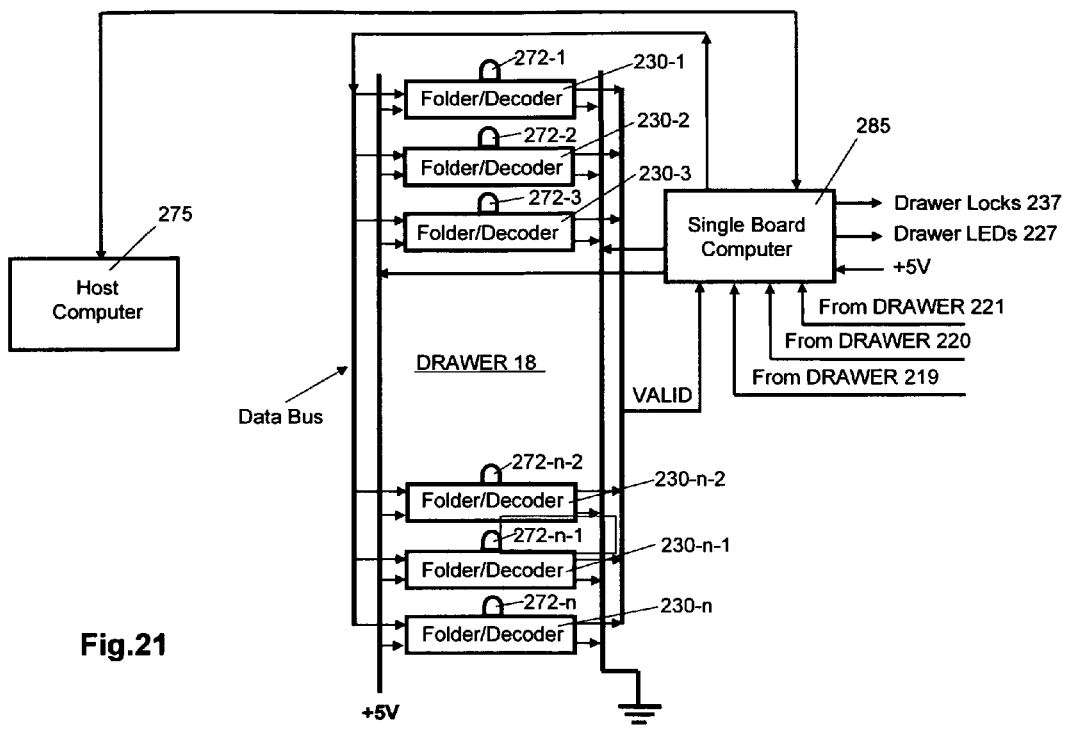
FIG. 21 is a schematic top plan view of a single drawer and the major system components of the invention.

FIG. 21 is a schematic top plan view of a single drawer 218 and the major system components of the invention showing the manner in which a plurality of folder circuits can be physically arranged in a single file drawer. As seen in this FIG., each folder 230-1, 230-2, . . . 230-n is supported in the drawer in such a manner that the appropriate electrical connections described above are made with the Data bus, +5V, Ground, and VALID signal conductors of the upper support members 228, 229. The Data bus, +5V, Ground, and VALID signal conductors are connected to a single board computer 285 shown in FIG. 22.

Figure 22:
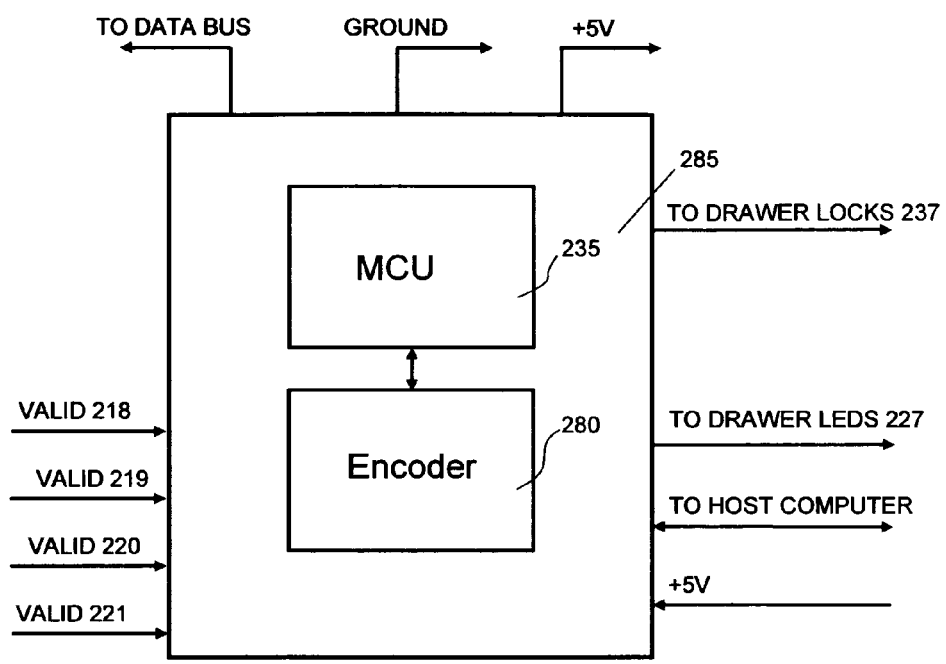
FIG. 22 is a schematic block diagram of the single board computer for a single file cabinet.

FIG. 22 is a schematic block diagram of the single board computer 285 for a single file cabinet 210 operationally connected to the system. As seen in this FIG., single board computer 285 comprises a microcomputer 235 and an encoder 280, both described above, with inputs and outputs as shown. Each file cabinet 210 is supplied with one single board computer 285. Optionally, each single board computer 285 may be provided with a unique identifying address in the system, for identification and maintenance purposes.

Each single board computer 285 comprising the elements shown in FIG. 22 supplies file folder address signals received from a host computer and encoded by an address encoder 280 located in single board computer 285 to all of the decoder circuits 270 incorporated into the primary support braces 240 of each folder 230-1, 230-2, . . . 230-n in the associated file cabinet 210i. Whenever a file folder address signal matches the address encoded into a decoder circuit 270 located in a given folder 230-1, 230-2, . . . 230-n in a given drawer in a given file cabinet 210i, a VALID signal is generated by the decoder circuit 270 of the targeted folder and is coupled to the single board computer 285 in the associated file cabinet 210i. In response to the receipt of a VALID signal, the corresponding single board computer 285 generates an operating signal for the drawer lock 237 of the appropriate drawer and activates the drawer LED 227 of the appropriate drawer in the file cabinet. In addition, the single board computer 285 generates a signal which is transmitted back to the host computer indicating that the file folder has been found and identifying the drawer and file cabinet in which the file folder with the correct address is located. As signified by the legended inputs "From DRAWER 219", "From DRAWER 220", and "From DRAWER 221", single board computer 285 responds to a VALID signal from each of these other drawers by generating a signal which is transmitted back to the host computer indicating that the file folder has been found and identifying the drawer and file cabinet in which the file folder with the correct address is located. Upon receipt of this information, host computer updates the information stored therein by comparing the drawer and file cabinet information received from single board computer 285 with the same information stored in memory, changing the information as necessary, and terminating the object address signals originally transmitted to single board computer 285.

To find a file folder in the system, the operator enters the basic file information into the system host computer, which contains a complete list of file folder addresses, as well as the drawer number and file cabinet ID in which each addressable file folder is purportedly located. The system host computer transmits a file folder request to the single board computer 285 in all of the file cabinets 210i, and the single board computers 285 in all of the file cabinets 210i in the system place the specified file folder address on the Data Busses of their respective file cabinets 210i. If the sought file folder is actually located in a given drawer, the single board computer 285 in the associated file cabinet 210i receives a VALID signal from the decoder circuit 270 whose address matches the address requested by host computer, generates the control signals described above for the appropriate drawer lock 237 and drawer front LED 227, and transmits back to the host computer the file cabinet and drawer information noted above. Should an operator open the drawer having the illuminated drawer front LED 227, the correct file folder would be indicated by the illuminated file folder LED 272i. If the file cabinet information or drawer location information (or both) do not match the same information stored in the memory of the host computer, this information is updated by the host computer. In the event that there is no file folder 230i operationally installed in the collection of file cabinets 210i whose address matches that of the requested address, the host computer will note the absence of a response to the file folder address inquiry and mark its records accordingly.

Once a file folder has been found by the file folder location system elements, the local microcomputer 145 transmits this event to the system host computer. In response, the system host computer generates document identifier signals and transmits these signals to the RFID reader 243 located in the file cabinet 210 containing the found file folder 230. RFID reader 243 generates an R.F. document tag interrogation signal, which is transmitted by RFID reader antenna 244 to all documents within the drawer containing the found file folder 230. If the document corresponding to the document identifier signals is present in any of the file folders contained in the drawer, the RFID tag associated to that document will respond to the interrogation signal from RFID reader 243 according to the RFID protocol implemented. For example, the tag can respond by transmitting a signal containing the tag identification information, followed by the contents of that document. When RFID reader 243 receives this information via RFID reader antenna 244, it relays this information to the system host computer for further use. If no response is received by RFID reader 243 within a preselected period of time, RFID reader 243 may repeat the transmission to the RFID reader antenna 244, or transmit a document not found signal back to the system host computer, depending on the system protocol established.

The integrity of the entire collection of file folders 230i can be quickly checked by operating the host computer in the sweep address mode. As the addresses are swept over the entire range of possible addresses, all file folder circuits which are operationally present in the collection of file cabinets 210i will respond with a VALID signal and this will be detected by the corresponding single board computer 285 and transmitted back to the host computer. The address of any missing or non-functioning file folder 230*i* will not result in the generation of a VALID signal, and this lack of response will be detected by the system host computer. This absence of an operational file folder 230*i* of a given specific address can be correlated by the system host computer to the file folder identification in the system host computer by noting the addresses of the non-responsive file folder circuits.

Similarly, the integrity of the entire collection of documents in the system can be checked by operating the system host computer to generate sequentially the document identifier signals for all documents registered in the system. The host computer initially sends each document identifier signal to the RFID reader 243 in the file cabinet 210 in which the document corresponding to the document identifier signal supposedly resides (according to the system master list). The RFID reader 243 in that file cabinet 210 then generates an interrogation signal and waits for a response. If a response is received, this event is transmitted by the RFID reader 243 back to the system host computer as a document found signal. If no response to the interrogation signal is received, this event is transmitted by the RFID reader 243 back to the system host computer as a document not found signal. The system host computer may proceed at that point to re-send the same document identifier signal to the RFID reader 243 in the same file cabinet 210 with an instruction to transmit a document interrogation signal to the documents in a different drawer of that file cabinet 210. If a document found signal results, the system host computer will update the system records to note the new drawer location of the document. If no document found signal results from the interrogation of all documents in all drawers of the originally selected cabinet 210, the system host computer may proceed at that point to sequentially send the same document identifier signal to all file cabinets 210 in the system and wait for responses from the RFID readers 243 in the other file cabinets. If no document found response is received, the system host computer can then add that document to a missing documents list. If a document found response is received from one of the cabinets 210 in the system, the system host computer can update the master list of documents to note the new location of the document.

The system may be initially configured in the same manner as that discussed above in connection with the R.F. file folder and R.F. document location and retrieval system.

Figure 23:
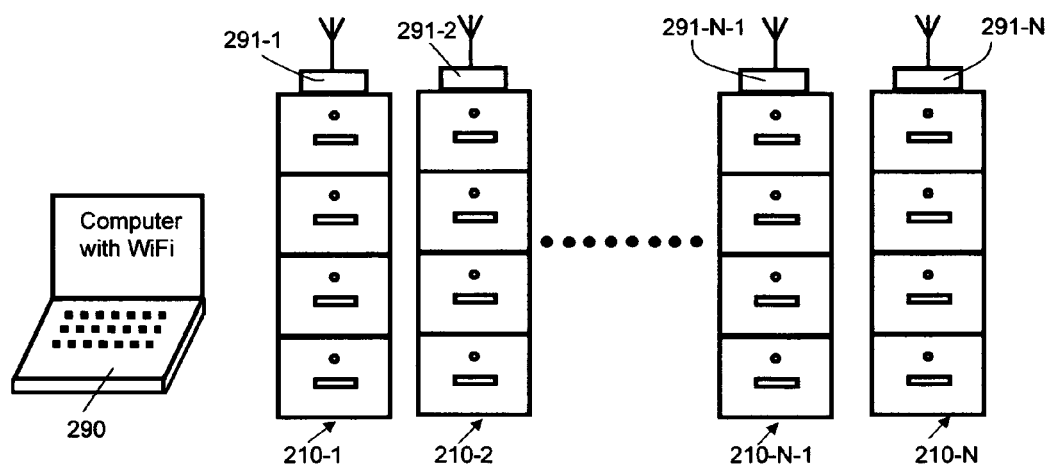
FIG. 23 is a schematic perspective view of a multiple file cabinet arrangement in a wireless implementation of the invention

FIG. 23 illustrates an alternate embodiment of the document management system implementation of the invention using wireless communication between the individual file cabinets 210*i* and a system host computer 290. As seen in this FIG., each cabinet 210*i* is provided with a WIFI transceiver 291*i* for communication with a host computer 290 similarly equipped. WIFI transceivers 291*i* are preferably commercially available units which have already undergone and passed radiation testing, such as a Wibox wireless device server unit available from Lantronix Inc. of Irvine, Calif. The host computer 290 is provided with a matching internal WIFI transceiver. Operation of the FIG. 23 system is essentially identical to that of the system of FIGS. 16-22, with the exception that the file folder identification signals are transmitted to file cabinets 210*i* using wireless transmission and the file cabinet and drawer information signals are transmitted to host computer 290 using wireless transmission, rather that the hard wired connections of the embodiment of FIGS. 16-22. In addition, there may be additional security considerations to the wireless embodiment of FIG. 23 in order to prevent unauthorized transmission and reception, and interception, of the WIFI signals.

Tag collision in RFID systems can happen when multiple tags are energized by the RFID tag reader simultaneously and reflect their respective signals back to the reader at the same time. This problem often occurs when a large number of tags must be read together in the same R.f. field. In order to minimize the probability of tag collision in systems incorporating the invention, several cautionary steps should be taken. The RFID reader antenna 144, 244 should have a relatively low Q factor, and the reader should be operated in a higher power mode, such as 10 watts. The tag locations on the documents should be staggered or randomly located, as discussed above with reference to FIG. 5. A stack tag system, such as the PJM un-tune stack tags noted above (Infineon SRF 66V10ST) should be used with the documents.

When implementing the system of FIGS. 7-15 using the R.F. file folder search technique, consideration should be given to the R.F. frequency ranges employed for the crystals, and the choice of R.F. carrier frequency for the RFID reader. Most standard RFID readers in use today operate at a frequency of 13.56 mHz. The preferred range of frequencies for the crystals as noted above is from about 2.0-20.0 mHz. Crystal frequencies near the 13.56 mHz. value should be avoided in order to preclude any interference between the two R.F. systems. One solution is to limit the crystal range to a maximum of 10.0 mHz. Other solutions will occur to those of ordinary skill in the art.

The document remote location and retrieval technique described above affords several advantages over known document management systems. Firstly, it eliminates the need for a human operator to physically find the correct file cabinet and drawer, and physically remove the document and transport it to a destination site, since the document, once located, can be remotely read and printed out (as necessary). In addition, in those cases in which the actual document must be physically transported to a user site, the document—if still somewhere in the system—can be quickly found using the serial file folder search and document search techniques. Also, the integrity of the document management system can be thoroughly tested remotely to find mis-filed documents and to identify documents missing from the system.

Although the above provides a full and complete disclosure of the preferred embodiments of the invention, various modifications, alternate constructions and equivalents will occur to those skilled in the art. For example, while the invention has been described with reference to specific R.F. frequencies, other frequencies may be employed, depending on the preferences of the system designer. Moreover, while the indicators have been described as visible indicators, other types of indicators, such as audible indicators, may be used, if desired. In addition, while the invention has been primarily described with reference to a single file cabinet, it is understood that the invention may be implemented using multiple file cabinets as shown in FIG. 23 positioned at the same or different locations in an office. Further, the invention may be used to manage a document management system of many cabinets positioned at different physical locations using an internal or an external computer network, if desired. Therefore, the above should not be construed as limiting the invention, which is defined by the appended claims.

What is claimed is:

1. A method of remotely locating and retrieving a document physically located in a file folder in a file cabinet in a document storage system having a host computer, a master list of documents, file folders in which individual documents are registered, and file cabinets in which file folders are located, each file cabinet having a control unit, said method comprising the steps of:

(a) using the host computer to designate a document to be found;

(b) transmitting a file folder request from the host computer directly to the control unit of the file cabinet in which the file folder containing the document is located according to the master list;

(c) using the control unit to locally search the file cabinet for the file folder identified in the request;

(d) using the control unit to transmit a file folder found signal directly to the host computer when the file folder is found;

(e) transmitting a document identifier signal from the host computer directly to the control unit of the file cabinet containing the found file folder;

(f) using the control unit to locally search the found file folder for the document specified by the document identifier signal; and (g) using the control unit to transmit the contents of the found document directly to the host computer when the document specified by the document identifier signal has been found so that physical presence of a human operator at the file cabinet location is not necessary to remotely retrieve the found document to the location of the host computer.

2. The method of claim 1 wherein the step (a) of using is performed by keyboard entry of the document designation information into the host computer containing the master list.

3. The method of claim 1 wherein the step (b) of transmitting said file folder request is performed over a communication link.

4. The method of claim 3 wherein the communication link is a wireless link.

5. The method of claim 1 wherein the step (c) is performed by the control unit using an R.F. search technique.

6. The method of claim 5 wherein the R.F. search technique includes the step of generating R.F. signals having a frequency matching the frequency of a crystal located in the file folder identified in the request.

7. The method of claim 1 wherein the step (c) is performed by the control unit using an address matching search technique.

8. The method of claim 7 wherein the address matching search technique includes the step of generating address signals having an address value matching the value of an address stored in a decoder circuit located in the file folder identified in the request.

9. The method of claim 1 wherein each document includes an RFID tag with a read-only-memory containing a document identifier and an electronic version of the document; and wherein the step (f) is performed by the control unit by generating R.F. document tag interrogation signals containing the document identifier.

10. A document management system for enabling remote location and retrieval of documents, said system comprising:

a host computer;

a plurality of file cabinets having a plurality of file drawers;

a plurality of file folders located in said file drawers;

a plurality of documents located in said plurality of file folders, each document having an RFID tag containing a document identifier and an electronic copy of the contents of the document;

each file cabinet having a control unit for receiving file folder request signals directly from said host computer, performing a file folder search in response to receipt of said file folder request signal, and sending a response directly to said host computer indicating the result of the file folder search;

each file folder having a circuit responsive to a search initiated by said file folder request signal for generating a response signal when the file folder request signal matches the identity of the file folder;

each file cabinet further including an RFID reader for receiving a document request signal directly from said host computer, performing a document search in response to receipt of a document request signal, and sending the contents of a found document directly to said host computer so that physical presence of a human operator at the file cabinet location is not necessary to remotely retrieve the found document to the location of the host computer.

11. The system of claim 10 wherein said control unit includes an R.F. signal generator for generating search signals having a frequency component; and wherein said file folder circuit has a crystal with a specific resonant frequency so that said response signal is generated when the frequency component of a search signal matches the resonant frequency of the crystal.

12. The system of claim 10 wherein said control unit includes an address encoder for generating a file folder address signal in response to the receipt of said file folder request signal; and wherein said file folder circuit has an address decoder containing a unique address so that said response signal is generated when the address signal generated by said address encoder matches the unique address.

* * * * *

UNITED STATES PATENT AND TRADEMARK OFFICE
CERTIFICATE OF CORRECTION

PATENT NO. : 8,994,534 B2  
APPLICATION NO. : 12/803712  
DATED : March 31, 2015  
INVENTOR(S) : Shengbo Zhu et al.

It is certified that error appears in the above-identified patent and that said Letters Patent is hereby corrected as shown below:

on the title page, item (73) change "ZMicrodata" to "iMicrodata"

Signed and Sealed this
Second Day of June, 2015

Michelle K. Lee
*Director of the United States Patent and Trademark Office*